Figure 1:
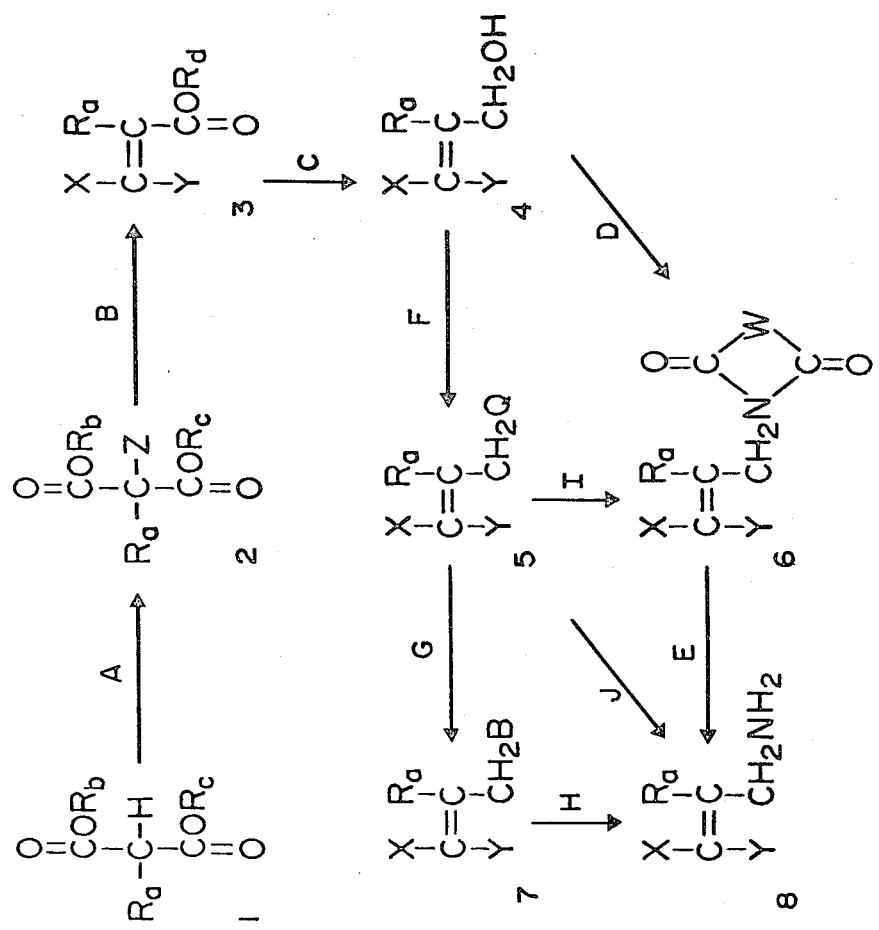
Figure 2:
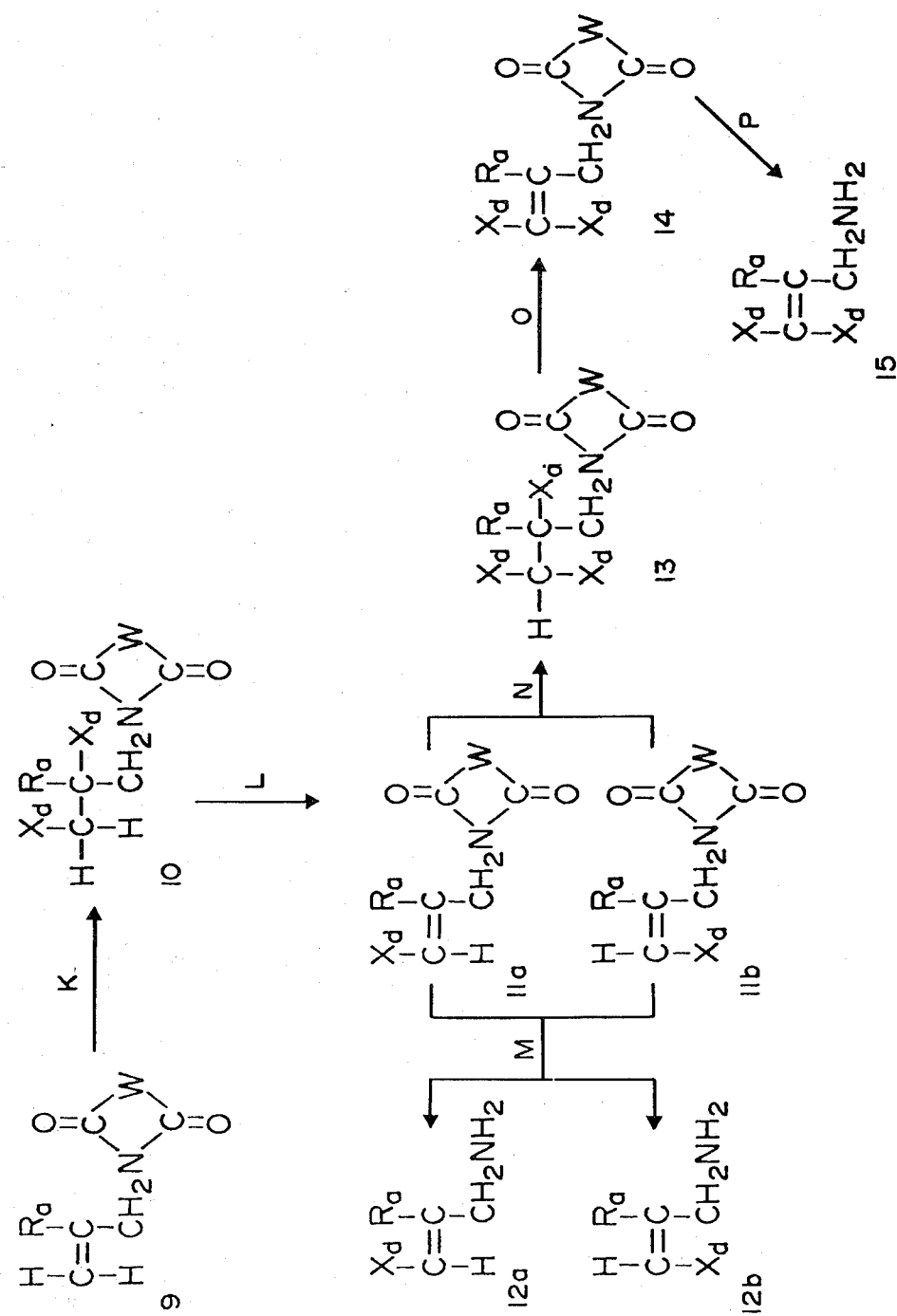

United States Patent [19]

Bey

[11] 4,454,158
[45] Jun. 12, 1984

[54] ALLYL AMINE MAO INHIBITORS

[75] Inventor: Philippe Bey, Strasbourg, France

[73] Assignee: Merrell Toraude et Compagnie, Strasbourg, France

[21] Appl. No.: 268,555

[22] Filed: Jun. 1, 1981

[51] Int. Cl.$^3$ ............................................. A01N 33/02
[52] U.S. Cl. ................................... 424/330; 546/229; 549/49; 549/55; 549/74; 549/469; 549/491; 564/383; 568/335; 568/775; 548/511; 548/560
[58] Field of Search .................. 564/383; 260/326.15, 260/326.9, 346.73, 347.7; 546/229; 549/49, 55, 74; 568/335, 775

[56] References Cited

PUBLICATIONS

Tiffeneau et al. *Bull. Soc. Chim.* 2 1876 (1935).
Patanova, I. *Izv Vyssh, Uchobn Zaved, Khim Khim Technol* 18, 531 (1975).
Schulze, K. et al., *Z. Chem.* 17 58 (1977).
Rando, R. *J. Am. Chem. Soc.* 95 4438 (1975).
Rando, R. et al., *Molecular Pharmacology* 13 1005 (1977).
Boor, P. et al., *Amer. J. Pathol.* 100, 739 (1980).
Krantz, A. et al., Drug Action and Design: *Mechanism-Based Enzyme Inhibitor*, pp. 145–174 Ekener N. Holland N.Y. 1979.

*Primary Examiner*—Paul J. Killos
*Attorney, Agent, or Firm*—Gary D. Street; Stephen L. Nesbitt; Raymond A. McDonald

[57] ABSTRACT

Compounds of the formula $$\begin{array}{cc} X & R \\ | & | \\ C=C \\ | & | \\ Y & CH_2NHR_1 \end{array} \quad \text{or} \quad \begin{array}{cc} X & A-R \\ | & | \\ C=C \\ | & | \\ Y & CH_2NHR_1 \end{array}$$

I  II wherein:
R is phenyl, phenyl monosubstituted, disubstituted, or trisubstituted by ($C_1$–$C_8$) alkyl, ($C_1$–$C_8$)alkoxy, hydroxy, chlorine, bromine, iodine, fluorine, trifluoromethyl, nitro, ($C_1$–$C_6$)alkylcarbonyl, benzoyl, or phenyl; 1-, or 2-naphthyl; 1-, 2-, or 3-indenyl; 1-, 2-, or 9-fluorenyl; 1-, 2-, or 3-piperidinyl; 2- or 3-pyrrolyl; 2- or 3-thienyl; 2- or 3-furanyl; 2- or 3-indolyl; 2- or 3-thianaphthenyl; or 2- or 3-benzofuranyl;
$R_1$ is hydrogen, ($C_1$–$C_8$)alkyl, benzyl, or phenethyl;
X and Y independently, are hydrogen, fluorine, chlorine, or bromine; and
A is a divalent radical of the formula:

$$-(CH_2)_m-\overset{R_2}{\underset{|}{CH}}(CH_2)_n-,$$

wherein $R_2$ is hydrogen, methyl, or ethyl, and m and n, independently, are an integer from 0 to 4, provided that m+n cannot be greater than 4; $-(CH_2)_p-D-(CH_2)_q-$, wherein D is oxygen, or sulfur, p is an integer from 2 to 4, and q is an integer from 0 to 2, provided that p+q cannot be greater than 4; or $-(CH_2)_r-CH=CH(CH_2)_s-$, wherein r is an integer from 1 to 3 and s is an integer from 0 to 2, provided that r+s cannot be greater than 3;

or a non-toxic, pharmaceutically-acceptable acid addition salt thereof; provided that when each of X and Y in Formula I is hydrogen, R cannot be phenyl;

are MAO inhibitors useful for treating depression. Processes and intermediates for preparing the compounds of Formula I or II are also described.

68 Claims, 2 Drawing Figures

SCHEME I
Fig. I

SCHEME II

ALLYL AMINE MAO INHIBITORS

This invention relates to novel chemical compounds, to intermediates for their production, and to pharmaceutical compositions and methods of treatment employing said compounds.

The class of compounds known as monoamine oxidase inhibitors (MAO inhibitors) has been employed in psychiatry for over 20 years for the treatment of depression, [See Goodman and Gilman, *The Pharmacological Basis of Therapeutics,* 6th Ed, McMillan Publishing Co., Inc., N.Y., 1980, pages 427–430]. MAO Inhibitors currently used in the USA for treating depression are tranylcypromine (PARNATE, SKF), phenelzine (NARDIL, Parke-Davis), and isocarboxazid (MARPLAN, Roche). In addition, another MAO inhibitor, pargyline (EUTRON, Abbott), is available for the treatment of hypertension [See *Physicians' Desk Reference,* 34th Ed., Medical Economics Co., Oradell, N.J., 1980, pages 1327–1328 (phenelzine), pages 1466–1468 (isocarboxazid), pages 1628–1630 (tranylcypromine) and pages 521–522 (pargyline)]. In addition for being used in treating depression, MAO inhibitors can be employed to treat other psychiatric disorders, such as phobic anxiety states.

It is believed that the MAO inhibitors act to alleviate psychiatric disorders, such as depression, by increasing the concentration of one or more biogenic monoamines in the brain or sympathetic nervous system. The monoamine oxidase enzyme (MAO) plays an important role in the metabolic regulation of the monoamines since it catalyzes the biodegradation of the monoamines through oxidative deamination. By inhibiting MAO, the degradation of the monoamines is blocked, and the result is an increase in the availability of the monoamines for their physiological functions. Among the physiologically active monoamines which are known substrates for MAO are: (a) the so-called "neurotransmitter" monoamines, such as the catecholamines (e.g. dopamine, epinephrine, and norepinephrine) and the indoleamines (e.g. tryptamine and 5-hydroxytryptamine), (b) the so-called "trace" amines (e.g. o-tyramine, phenethylamine, tele-N-methylhistamine), and (c) tyramine.

The usefulness of the MAO inhibitors in treating depression is limited because the administration of such agents can potentiate the pharmacological actions of certain food substances or drugs leading to dangerous and sometimes lethal effects. For example, persons receiving an MAO inhibitor must avoid the ingestion of foods which have a high tyramine content (such as cheese) because the MAO inhibitor will block the metabolic degradation of tyramine in the gut to produce high circulating levels of tyramine, consequent release of catecholamines in the periphery, and finally serious hypertension. The potentiation by a MAO inhibitor of the pressor effect of tyramine arising from the ingestion of cheese, and the hypertensive episode produced thereby, are commonly known as the "cheese reaction" or "cheese effect". Moreover, persons on conventional MAO therapy can not be given directly-acting sympathomimetic drugs (or precursors thereof) which are themselves substrates for MAO (e.g. dopamine, epinephrine, norepinephrine, or L-DOPA) and of indirectly-acting sympathomimetic drugs (e.g. amphetamines or cold, hay-fever, or weight control preparations that contain a vasoconstrictor). The potentiation of the pressor effects of indirectly-acting sympathomimetic drugs is especially profound. This is because such drugs act peripherally primarily by releasing catecholamines in nerve endings, and the concentration of the liberatated catecholamines will be dangerously elevated if the metabolic degradation of the catecholamines via MAO is blocked. In addition, a MAO inhibitor should not be used in combination with another MAO inhibitor or with hypotensive agents, dibenzazepine antidepressants, meperidine, CNS depressants, and anticholinergic agents.

Biochemical and pharmacological studies indicate that the MAO enzyme exists in two forms known as "MAO Type A" (MAO-A) and "MAO Type B" (MAO-B). The two forms differ in their distribution in body organs, in their substrate specificity, and in their sensitivity to inhibitors. In general, MAO-A selectively oxidizes the so-called "neurotransmitter" monoamines (epinephrine, norepinephrine, and 5-hyroxytryptamine) while MAO-B selectively oxidizes the "trace" monoamines (o-tyramine, phenethylamine, and tele-N-methylhistamine). Both MAO-A and MAO-B oxidize tyramine, tryptamine, and dopamine. However, in man, dopamine has been shown to be a preferred substrate for MAO-B. The forms also differ in their sensitivity to inhibition, and thus they can be preferentially inhibited depending upon the chemical structure of the inhibitor and/or the relative concentrations of the inhibitor and the enzyme. The MAO inhibitors currently sold in the USA for the therapy of depression (tranyclcypromine, phenelzine, and isocarboxazid) are not preferential in their action upon MAO. However, various chemical compounds are known in the art to be preferential inhibitors of MAO, the most important being clorgyline, pargyline, and L-deprenyl which are all reported to be clinically effective antidepressant agents. MAO-A is preferentially inhibited by clorgyline, while MAO-B is preferentially inhibited by pargyline and L-deprenyl. It should be observed that the "selectivity" of an MAO inhibitor arises because the inhibitor has a greater affinity for one form of the enzyme. Thus, the selectivity of an inhibitor for MAO-A or MAO-B in vivo will be dose-dependent, selectivity being lost as the dosage is increased. Clorgyline, pargyline, and L-deprenyl are selective inhibitors at lower dosages, but are not selective inhibitors at higher dosages. The literature concerning MAO-A and MAO-B, and the selective inhibition thereof, is extensive. [See, for example, Goodman and Gilman, ibid, pages 204–205; Neff et al, Life Sciences, 14, 2061 (1974); Murphy, *Biochemical Pharmacology,* 27, 1889 (1978); Knoll, Chapter 10, pages 151–171 and Sandler, Chapter 11, pages 173–181, in *Enzyme Inhibitors as Drugs,* M. Sandler, Ed., Macmillan Press Ltd., London, 1980; Lipper et al, *Psychopharmacology,* 62, 123 (1979); Mann et al, Life Sciences, 26, 877 (1980); and various articles in *Monoamines Oxidase: Structure, Function and Altered Functions,* T. Singer et al Ed., Academic Press, N.Y., 1979].

Of the selective inhibitors of MAO, L-deprenyl is of interest since the "cheese effect" is not observed at the low dosages where preferential inhibition of MAO-B occurs. [See, Knoll, TINS, pages 111–113, May 1979]. This observation is not unexpected since the intestinal mucosa contains predominantely MAO-A which, because it is not inhibited, permits oxidation and removal of the ingested tyramine. The selectivity of L-deprenyl for MAO-B may account for its ability to potentiate L-DOPA for the treatment of Parkinson's disease without producing peripheral side effects, such as hypertension due to potentiation of pressor catecholamines [See Lees et al, Lancet, pages 791–795, Oct. 15, 1977 and Birkmeyer, Lancet, pages 439–443, Feb. 26, 1977].

In its first composition of matter aspect, this invention comprehends pharmacologically active compounds of the formulae:

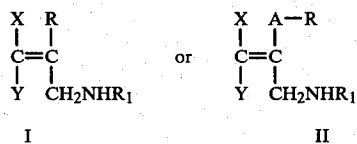

wherein:
R is phenyl; phenyl monosubstituted, disubstituted, or trisubstituted by ($C_1$–$C_8$)alkyl, ($C_1$–$C_8$)alkoxy, hydroxy, chlorine, bromine, iodine, fluorine, trifluoromethyl, nitro, ($C_1$–$C_6$)alkylcarbonyl, benzoyl, or phenyl; 1- or 2-naphthyl; 1-, 2-, or 3-indenyl; 1-, 2-, or 9-fluorenyl; 1-, 2-, or 3-piperidinyl; 2- or 3-pyrrolyl; 2- or 3-thienyl; 2- or 3-furanyl; 2- or 3-indolyl; 2- or 3-thianaphthenyl; or 2-or 3-benzofuranyl.

$R_1$ is hydrogen, ($C_1$–$C_8$)alkyl, benzyl, or phenethyl; X and Y, independently, are hydrogen, fluorine, chlorine, or bromine; and A is a divalent radical of the formula:

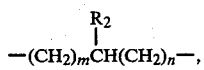

wherein $R_2$ is hydrogen, methyl, or ethyl, and m and n, independently, are an integer from 0 to 4, provided that m+n cannot be greater than 4; —$(CH_2)_p$—D—$(CH_2)_q$—, wherein D is oxygen or sulfur, p is an integer from 2 to 4, and q is an integer from 0 to 2, provided that p+q cannot be greater than 4; or —$(CH_2)_r$CH=CH$(CH_2)_s$—, wherein r is an integer from 1 to 3 and s is an integer from 0 to 2, provided that r+s cannot be greater than 3;
or a non-toxic, pharmaceutically-acceptable acid addition salt thereof; provided that when each of X and Y in Formula I is hydrogen, R cannot be phenyl.

The compounds of Formula I or II are pharmacologically active, being capable of inhibiting MAO as demonstrated in standard biological test procedures performed in vitro or in vivo in laboratory animals. The compounds of Formula I or II are useful for the treatment of psychiatric disorders, in particular depression, which are known to be responsive to MAO inhibitor therapy. For the treatment of depression, the compounds can be employed in a manner similar to that of the known clinically active MAO inhibitors, such as phenelzine and tranylcypromine.

Certain compounds of Formula I or II are capable of preferentially inhibiting the B form of MAO in vitro and, at suitable low dosages in vivo, such compounds will inhibit MAO-B without substantially inhibiting MAO-A. At dosage levels where such compounds exert a selective effect on MAO-B, the compounds will not produce a marked "cheese effect". Hence, as with L-deprenyl, a known selective inhibitor of MAO-B, such compounds can be employed at suitable dosages for the treatment of depression, or for the potentiation of L-DOPA in the treatment of Parkinsonism, with a significantly decreased risk of producing side effects, such as the "cheese effect". The compounds of Formula I or II which have been found to be selective inhibitors of MAO-B and to have a significantly decreased risk of producing the "cheese effect" are (E)-2-(4'-methoxyphenyl)-3-fluoroallylamine and (E)-2-(3',4'-dimethoxyphenyl)-3-fluoroallylamine, both of which are the most preferred embodiments of Formula I or II.

In its second composition of matter aspect, the present invention comprehends chemical compounds of the Formula

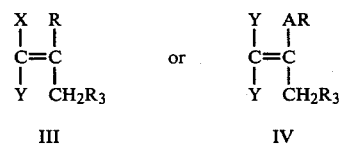

wherein X, Y, R, and A have the meanings defined supra with respect to Formua I or II, except that R cannot be mono-, di-, or tri-hydroxyphenyl, and $R_3$ is hydroxy or a leaving group. The compounds of Formula III and IV are intermediates for the preparation of the pharmacologically active compounds of Formula I and II, respectively. Preferred examples of leaving groups as defined by $R_3$ are: chlorine, bromine, tosyloxy, or mesyloxy. Other suitable leaving groups will be apparent to those skilled in the art of chemistry.

As employed herein, the term "alkyl" contemplates both straight and branched-chain alkyl groups. Straight-chain alkyl groups are preferred. Illustrative examples of ($C_1$–$C_8$)alkyl groups are methyl, ethyl, n-propyl, iso-propyl, n-butyl, iso-butyl, tert-butyl, n-pentyl, n-hexyl, n-heptyl, and n-octyl. Methyl and ethyl are most preferred. The term "alkoxy" contemplates both straight and branched-chain alkoxy groups. Straight-chain alkoxy groups are preferred. Illustrative examples of ($C_1$–$C_8$)alkoxy groups are methoxy, ethoxy, n-propoxy, iso-propoxy, n-butoxy, iso-butoxy, tert-butoxy, n-pentyloxy, n-hexyloxy, n-heptyloxy, and n-octyloxy. Methoxy and ethoxy are most preferred. The term "alkylcarbonyl" contemplates both straight- and branched-chain alkylcarbonyl groups. Straight-chain alkylcarbonyl groups are preferred. Illustrative ($C_1$–$C_6$)alkylcarbonyl groups are acetyl, propionyl, and n-butyryl. Acetyl is most preferred. The term "monosubstituted" as used herein in the definition of R in Formula I or II means that the phenyl ring is substituted by one substituent group which can be located at any of the available positions in the ring (i.e. in the ortho, para, or meta positions). The term "disubstituted" means that the phenyl ring is substituted by two substituent groups which may be located at any of the available positions in the ring or oriented in any manner with respect to each other. The term "trisubstituted" means that the phenyl ring is substituted by three substituent groups which may be located at any of the available positions in the ring or oriented in any manner with respect to each other. When R in Formula I or II represents a di- or tri-substituted phenyl group, the groups substituted on the phenyl ring may be the same or they may be different.

Illustrative examples of divalent groups represented by A are —$CH_2$—, —$(CH_2)_2$—, —$(CH_2)_3$—, —$(CH_2)_4$—, —$(CH_2)_5$—, —$CH_2S$—$(CH_2)_2$—, —$CH_2O(CH_2)_2$—, and —CH=CH—$CH_2$—. Methylene is preferred.

It will be apparent to those skilled in the art that, because the compounds of Formula I, II, III, or IV contain a double bond, depending on the meanings given to X and Y, geometric isomerism is possible. It should be understood, therefore, that in Formula I or II, a group represented by Y is oriented in the position trans to the group represented by —R or —AR, while a group represented by X is oriented in the position cis to a group represented by —R or —Ar. Thus, when X is fluorine, bromine, or chlorine and Y is hydrogen, Formula I or II depicts compounds wherein the halogen is oriented in the cis position with respect to the group represented by —R or —AR, and, when Y is fluorine, bromine, or iodine, and X is hydrogen, Formula I or II depicts compounds wherein the halogen is oriented in the trans position with respect to the groups represented by —R or —AR. The compounds in which the halogen is oriented in the cis position with respect to —R or —AR are preferred. In naming the compounds of Formula I, II, III, or IV herein, the prefixes "(E)" and "(Z)" are used in the conventionnal manner to indicate the stereochemistry at the double bond. If no stereochemical designation is given, both the substantially pure isomers, or mixtures thereof, are meant. The compounds of Formula I or II can be isolated either in the form of the free base or in the form of a non-toxic, pharmaceutically acceptable acid addition salt. Non-toxic, pharmaceutically acceptable acids suitable for preparing the acid addition salts are known in the art. The free bases can be converted to the acid addition salts, or the acid addition salts can be converted to the free bases, by conventionnal chemical methods.

Preferred compounds of Formula I or II are those wherein X is hydrogen and Y is fluorine; Y is hydrogen and X is fluorine; each of X and Y is fluorine; R is phenyl, or phenyl mono-, or di-, or tri-substituted by $(C_1-C_8)$alkyl, $(C_1-C_8)$alkoxy, hydroxy, chlorine, bromine, iodine, fluorine, trifluoromethyl, nitro, $(C_1-C_6)$alkylcarbonyl, benzoyl, or phenyl; $R_1$ is hydrogen, $(C_1-C_8)$alkyl, benzyl, or phenethyl; and A is a divalent alkylene radical of the formula $-(CH_2)_t-$, wherein t is an integer from 1 to 5. Hence, in its subgeneric aspects, the invention contemplates the following subclasses of compounds:

(i) A compound of Formula I wherein X is fluorine, Y is hydrogen, and $R_1$ is hydrogen.

(ii) A compound of Formula I wherein X is hydrogen, Y is fluorine, and $R_1$ is hydrogen.

(iii) A compound of Formula I wherein each of X and Y is fluorine, and $R_1$ is hydrogen.

(iv) A compound of Formula II wherein X is fluorine, Y is hydrogen, $R_1$ is hydrogen, and A is an alkylene radical of the formula $-(CH_2)_t-$ wherein t is an integer from 1 to 5.

(v) A compound of Formula II wherein X is hydrogen, Y is fluorine, $R_1$ is hydrogen, and A is an alkylene radical of the formula $-(CH_2)_t-$ wherein t is an integer from 1 to 5.

(vi) A compound of Formula II wherein each of X and Y is fluorine, $R_1$ is hydrogen, and A is an alkylene radical of the formula $-(CH_2)_t-$ wherein t is an integer from 1 to 5.

(vii) A compound as defined in paragraph (i), (ii), (iii), (iv), (v), or (vi) wherein R is phenyl.

(viii) A compound as defined in paragraph (i), (ii), (iii), (iv), (v), or (vi) above wherein R is phenyl mono-, di-, or tri-substituted by $(C_1-C_8)$alkyl, $(C_1-C_8)$alkoxy, hydroxy, chlorine, bromine, iodine, fluorine, trifluoromethyl, nitro, $(C_1-C_6)$alkylcarbonyl, benzoyl, or phenyl.

(ix) A compound as defined in paragraph (i), (ii), (iii), (iv), (v), or (vi) above wherein R is phenyl monosubstituted by $(C_1-C_8)$alkoxy, hydroxy or chlorine.

(x) A compound as defined in paragraph (i), (ii), (iii), (iv), (v), or (vi) above wherein R is phenyl di-substituted by $(C_1-C_8)$alkoxy, hydroxy or chlorine.

The most preferred compounds of Formula I, as defined in each of paragraphs (i), (ii), (iii), (vii), (viii), and (ix) above, are those wherein $R_1$ is hydrogen; and R is phenyl, methoxyphenyl, dimethoxyphenyl, hydroxyphenyl, dihydroxy phenyl, chlorophenyl, or dichlorophenyl. The most preferred compounds of Formula II, as defined in each of paragraphs (iv), (v), (vi), (vii), (viii), and (ix) above are those wherein $R_1$ is hydrogen, R is phenyl, methoxyphenyl, dimethoxyphenyl, hydroxyphenyl, dihydroxyphenyl, chlorophenyl, or dichlorophenyl, and A is methylene.

Illustrative examples of the compounds of Formula I are:

2-phenyl-3-fluoroallylamine,
2-(2'-methoxy)phenyl-3-fluoroallylamine,
2-(3'-methoxy)phenyl-3-fluoroallylamine,
2-(4'-methoxy)phenyl-3-fluoroallylamine,
2-(2',3'-dimethoxy)phenyl-3-fluoroallylamine,
2-(2',4'-dimethoxy)phenyl-3-fluoroallylamine,
2-(2',5'-dimethoxy)phenyl-3-fluoroallylamine,
2-(2',6'-dimethoxy)phenyl-3-fluoroallylamine,
2-(3',4'-dimethoxy)phenyl-3-fluoroallylamine,
2-(3',5'-dimethoxy)phenyl-3-fluoroallylamine,
2-(2'-hydroxy)phenyl-3-fluoroallylamine,
2-(3'-hydroxy)phenyl-3-fluoroallylamine,
2-(4'-hydroxy)phenyl-3-fluoroallylamine,
2-(2',3'-dihydroxy)phenyl-3-fluoroallylamine,
2-(2',4'-dihydroxy)phenyl-3-fluoroallylamine,
2-(2',5'-dihydroxy)phenyl-3-fluoroallylamine,
2-(2',6'-dihydroxy)phenyl-3-fluoroallylamine,
2-(3',4'-dihydroxy)phenyl-3-fluoroallylamine,
2-(3',5'-dihydroxy)phenyl-3-fluoroallylamine,
2-phenyl-3,3-difluoroallylamine,
2-(2'-methoxy)phenyl-3,3-difluoroallylamine,
2-(3'-methoxy)phenyl-3,3-difluoroallylamine,
2-(4'-methoxy)phenyl-3,3-difluoroallylamine,
2-(2',3'-dimethoxy)phenyl-3,3-difluoroallylamine,
2-(2',4'-dimethoxy)phenyl-3,3-difluoroallylamine,
2-(2',5'-dimethoxy)phenyl-3,3-difluoroallylamine,
2-(2',6'-dimethoxy)phenyl-3,3-difluoroallylamine,
2-(3',4'-dimethoxy)phenyl-3,3-difluoroallylamine,
2-(3',5'-dimethoxy)phenyl-3,3-difluoroallylamine,
2-(2'-hydroxy)phenyl-3,3-difluoroallylamine,
2-(3'-hydroxy)phenyl-3,3-difluoroallylamine,
2-(4'-hydroxy)phenyl-3,3-difluoroallylamine,
2-(2',3'-dihydroxy)phenyl-3,3-difluoroallylamine,
2-(2',4'-dihydroxy)phenyl-3,3-difluoroallylamine,
2-(2',5'-dihydroxy)phenyl-3,3-difluoroallylamine,
2-(2',6'-dihydroxy)phenyl-3,3-difluoroallylamine,
2-(3',4'-dihydroxy)phenyl-3,3-difluoroallylamine,
2-(3',5'-dihydroxy)phenyl-3,3-difluoroallylamine,
2-benzyl-3-fluoroallylamine,
2-(2'-methoxy)benzyl-3-fluoroallylamine,
2-(3'-methoxy)benzyl-3-fluoroallylamine,
2-(4'-methoxy)benzyl-3-fluoroallylamine,
2-(2',3'-dimethoxy)benzyl-3-fluoroallylamine,
2-(2',4'-dimethoxy)benzyl-3-fluoroallylamine,
2-(2',5'-dimethoxy)benzyl-3-fluoroallylamine,
2-(2',6'-dimethoxy)benzyl-3- fluoroallylamine,
2-(3',4'-dimethoxy)benzyl-3-fluoroallylamine,
2-(3',5'-dimethoxy)benzyl-3-fluoroallylamine,
2-(2'-hydroxy)benzyl-3-fluoroallylamine, 2-(3'-hydroxy)benzyl-3-fluoroallylamine,
2-(4'-hydroxy)benzyl-3-fluoroallylamine,
2-(2',3'-dihydroxy)benzyl-3-fluoroallylamine,
2-(2',4'-dihydroxy)benzyl-3-fluoroallylamine,
2-(2',5'-dihydroxy)benzyl-3-fluoroallylamine,
2-(2',6'-dihydroxy)benzyl-3-fluoroallylamine,
2-(3',4'-dihydroxy)benzyl-3-fluoroallylamine,
2-(3',5'-dihydroxy)benzyl-3-fluoroallylamine,
2-benzyl-3,3-difluoroallylamine,
2-(2'-methoxy)benzyl-3,3-difluoroallylamine,
2-(3'-methoxy)benzyl-3,3-difluoroallylamine,
2-(4'-methoxy)benzyl-3,3-difluoroallylamine,
2-(2',3'-dimethoxy)benzyl-3,3-difluoroallylamine,
2-(2',4'-dimethoxy)benzyl-3,3-difluoroallylamine,
2-(2',5'-dimethoxy)benzyl-3,3-difluoroallylamine,
2-(2',6'-dimethoxy)benzyl-3,3-difluoroallylamine,
2-(3',5'-dimethoxy)benzyl-3,3-difluoroallylamine,
2-(2'-hydroxy)benzyl-3,3-difluoroallylamine,
2-(3'-hydroxy)benzyl-3,3-difluoroallylamine,
2-(4'-hydroxy)benzyl-3,3-difluoroallylamine,
2-(2',3'-dihydroxy)benzyl-3,3-difluoroallylamine,
2-(2',4'-dihydroxy)benzyl-3,3-difluoroallylamine,
2-(2',5'-dihydroxy)benzyl-3,3-difluoroallylamine,
2-(2',6'-dihydroxy)benzyl-3,3-difluoroallylamine,
2-(3',4'-dihydroxy)benzyl-3,3-difluoroallylamine,
2-(3',5'-dihydroxy)benzyl-3,3-difluoroallylamine, Preferred compounds of Formula III or IV are those wherein X is hydrogen and Y is fluorine; X is fluorine and Y is hydrogen; each of X and Y is fluorine; R is phenyl, or phenyl mono-, di-, or tri-substituted by $(C_1-C_8)$alkyl, $(C_1-C_8)$alkoxy, chlorine, bromine, iodine, fluorine, trifluoromethyl, nitro, $(C_1-C_6)$alkylcarbonyl, benzoyl, or phenyl. Most preferred compounds of Formula III are those wherein R is phenyl, methoxyphenyl, dimethoxyphenyl, chlorophenyl, or dichlorophenyl. Most preferred compounds of Formula IV are those wherein R is phenyl, metoxyphenyl, dimethoxyphenyl, chlorophenyl, or dichlorophenyl and A is methylene.

Illustrative embodiements of Formula III or IV are:
2-phenyl-3-fluoroallyl alcohol,
2-benzyl-3-fluoroallyl alcohol,
2-(2'-methoxy)phenyl-3-fluoroallyl alcohol,
2-(3'-methoxy)phenyl-3-fluoroallyl alcohol,
2-(4'-methoxy)phenyl-3-fluoroallyl alcohol,
2-(2',3'-dimethoxy)phenyl-3-fluoroallyl alcohol,
2-(2',4'-dimethoxy)phenyl-3-fluoroallyl alcohol,
2-(2',5'-dimethoxy)phenyl-3-fluoroallyl alcohol,
2-(2',6'-dimethoxy)phenyl-3-fluoroallyl alcohol,
2-(3',4'-dimethoxy)phenyl-3-fluoroallyl alcohol,
2-(3',5'-dimethoxy)phenyl-3-fluoroallyl alcohol,
2-(2'-methoxy)benzyl-3-fluoroallyl alcohol,
2-(3'-methoxy)benzyl-3-fluoroallyl alcohol,
2-(4'-methoxy)benzyl-3-fluoroallyl alcohol,
2-(2',3'-dimethoxy)benzyl-3-fluoroallyl alcohol,
2-(2',4'-dimethoxy)benzyl-3-fluoroallyl alcohol,
2-(2',5'-dimethoxy)benzyl-3-fluoroallyl alcohol,
2-(2',6'-dimethoxy)benzyl-3-fluoroallyl alcohol,
2-(3',4'-dimethoxy)benzyl-3-fluoroallyl alcohol,
2-(3',5'-dimethoxy)benzyl-3-fluoroallyl alcohol,
2-phenyl-3,3-difluoroallyl alcohol,
2-benzyl-3,3-difluoroallyl alcohol,
2-(2'-methoxy)phenyl-3,3-difluoroallyl alcohol,
2-(3'-methoxy)phenyl-3,3-difluoroallyl alcohol,
2-(4'-methoxy)phenyl-3,3-difluoroallyl alcohol,
2-(2',3'-dimethoxy)phenyl-3,3-difluoroallyl alcohol,
2-(2',4'-dimethoxy)phenyl-3,3-difluoroallyl alcohol,
2-(2',5'-dimethoxy)phenyl-3,3-difluoroallyl alcohol,
2-(2',6'-dimethoxy)phenyl-3,3-difluoroallyl alcohol,
2-(3',4'-dimethoxy)phenyl-3,3-difluoroallyl alcohol,
2-(3',5'-dimethoxy)phenyl-3,3-difluoroallyl alcohol,
2-(2'-methoxy)benzyl-3,3-difluoroallyl alcohol,
2-(3'-methoxy)benzyl-3,3-difluoroallyl alcohol,
2-(4'-methoxy)benzyl-3,3-difluoroallyl alcohol,
2-(2',3'-dimethoxy)benzyl-3,3-difluoroallyl alcohol,
2-(2',4'-dimethoxy)benzyl-3,3-difluoroallyl alcohol,
2-(2',5'-dimethoxy)benzyl-3,3-difluoroallyl alcohol,
2-(2',6'-dimethoxy)benzyl-3,3-difluoroallyl alcohol,
2-(3',4'-dimethoxy)benzyl-3,3-difluoroallyl alcohol,
2-(3',5'-dimethoxy)benzyl-3,3-difluoroallyl alcohol, In its method of use aspect, the present invention provides a method for treating depression which comprises administering to a depressed patient an effective amount of a compound of the formula:

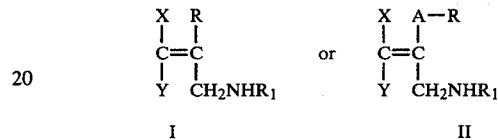

wherein:

R is phenyl, phenyl monosubstituted, disubstituted, or trisubstituted by $(C_1-C_8)$alkyl, $(C_1-C_8)$alkoxy, hydroxy, chlorine, bromine, iodine, fluorine, trifluoromethyl, nitro, $(C_1-C_6)$alkylcarbonyl, benzoyl, or phenyl; 1-, or 2-naphthyl; 1-, 2-, or 3-indenyl; 1-, 2-, or 9-fluorenyl; 1-, 2-, or 3-piperidinyl; 2- or 3-pirroyl; 2- or 3-thienyl; 2- or 3-furanyl; 2- or 3-indolyl; 2- or 3-thianaphtenyl; or 2- or 3-benzofuranyl;

$R_1$ is hydrogen, $(C_1-C_8)$alkyl, benzyl, or phenethyl; X and Y, independently, are hydrogen, fluorine, chlorine, or bromine; and A is a divalent radical of the formula:

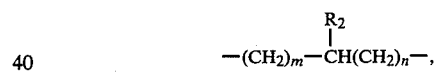

wherein $R_2$ is hydrogen, methyl, or ethyl, and m and n, independently, are an integer from 0 to 4, provided that $m+n$ cannot be greater than 4; —$(CH_2)_p$—D—$(CH_2)_q$—, wherein D is oxygen or sulfur, p is an integer from 2 to 4, and q is an integer from 0 to 2, provided that $p+q$ cannot be greater than 4; or —$(CH_2)_r$-CH=CH$(CH_2)_s$—, wherein r is an integer from 1 to 3 and s is an integer from 0 to 2, provided that $r+s$ cannot be greater than 3; and s is an integer from 0 to 2, provided that $r+s$ cannot be greater than 3;

or a non-toxic, pharmaceutically-acceptable acid addition salt thereof; provided that when each of X and Y in Formula I is hydrogen, R cannot be phenyl.

For pharmacological use, the compounds of Formula I or II may be administered in the form of an acid addition salt of a non-toxic organic or inorganic acid. Appropriate salts are those formed, for example, from the following acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, and benzenesulfonic.

When employed to treat depression, the effective dosage of the compounds of Formula I or II will vary according to the particular compound being employed, the severity and nature of the depression and the particular subject being treated. In general, effective results can be achieved by administering a compound at a dosage level of from about 5 mg to about 100 mg per day, given systemically. Therapy should be initiated at lower dosages, the dosage thereafter Formula I or II may be administered orally in solid dosage forms, e.g. capsules, tablets, or powders, or in liquid forms, e.g. solutions or suspensions. The compounds may also be injected parenterally in the form of sterile solutions or suspensions. Solid oral forms may contain conventional excipients, for instance: lactose, succrose, magnesium stearate, resins, and like materials. Liquid oral forms may contain various flavoring, coloring, preserving, stabilizing, solublizing or suspending agents. Parenteral preparations are sterile aqueous or nonaqueous solutions of suspensions which may contain various preserving, stabilizing, buffering, solubilizing, or suspending agents. If desired, additives, such as saline or glucose may be added to make the solutions isotonic.

At the dosage levels set forth above, the compounds of Formula I or II, in general, will inhibit both forms of MAO. At lower dosage levels, certain compounds of Formula I or II may preferentially inhibit MAO-B and may have a decreased risk of producing the "cheese effect". For example, (E)-2-(4'-methoxy)phenyl-3-fluoroallylamine or (E)-2-(3',4'-dimethoxy)phenyl-3-fluoroallylamine will selectively inhibit MAO-B at a systemic dosage range of about 0.1 mg to about 5 mg per day, and, at this dosage range, the risk of adverse reaction from the "cheese effect" will be substantially reduced or eliminated.

The manner and processes for preparing the compounds of Formula I or II will now be discussed with reference to the DRAWINGS. The compounds of Formula I and II wherein: (a) X and Y are each hydrogen; (b) X is fluorine, chlorine, or bromine and Y is hydrogen; and (c) X and Y are the same and are each fluorine, chlorine, or bromine; can be prepared in general by the process steps depicted in Scheme I of the DRAWINGS. In Scheme I the symbols $R_a$, $R_b$, $R_c$, $R_d$, $R_e$, B, Q, X, Y, W, and Z in the various formulae have the following meanings:

$R_a$ is R- or R-A-wherein R and A have the meanings defined with respect to Formulae I and II;

$R_b$ is tert-butyl, benzyl, diphenylmethyl, or triphenylmethyl;

$R_c$ is $C_1$-$C_4$ straight-chain alkyl, tert-butyl, benzyl, diphenylmethyl, or triphenylmethyl;

$R_d$ is hydrogen or straight-chain $C_1$-$C_4$ alkyl;

Z is a halomethyl group of the formula: —$CHFX_a$, —$CF_2X_a$, —$CH_2X_a$, —$CHClX_b$, —$CCl_2X_b$, —$CHBrX_c$, or —$CBr_2X_c$, wherein $X_a$ is fluorine, chlorine, bromine, or iodine; $X_b$ is chlorine, bromine, or iodine; and $X_c$ is bromine or iodine;

X and Y are, independently, hydrogen, fluorine, chlorine, or bromine;

Q is chlorine, bromine, iodine, benzenesulfonyloxy, p-toluenesulfonyloxy (tosyloxy), methylsulfonyloxy (mesyloxy), or other leaving group;

B is the hexamethylenetetrammonium group; a group of the formula —$NHCO_2R_e$ wherein $R_e$ is $C_1$-$C_4$ alkyl; or a group capable of generating a primary amino; and W is

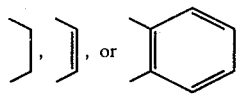

The process depicted in Scheme I comprises the following steps:
(1) Halomethylating a malonic acid diester of Formula (1) to form the halomethyl diester of Formula (2) [Step A].
(2) Hydrolysing the halomethyl diester under acidic conditions or catalytically hydrogenating the diester to cleave one or both of the ester groups and then treating the intermediate so-produced with a base, whereby the intermediate undergoes decarboxylation and elimination of a halide ion to form the acrylic acid or acrylate ester of Formula (3) [Step B].
(3) Reducing the acrylic acid or acrylate ester to form the allyl alcohol of Formula (4) [Step C].
(4) Replacing the hydroxy group of the allyl alcohol of Formula (4) with a primary amino group to form the allyl primary amine of Formula (8), via formation of intermediates of Formula (5), Formula (6), or Formula (7) ]Steps D-J].

The individual process steps shown in Scheme I, and described in general above, can be carried out using methods that are known or conventional in the art of chemistry. Examples of the methods that can be employed for carrying out the particular transformations depicted in Scheme I are described as follows:

In Step A, a diester of Formula (1) is halomethylated in known manner by first treating the diester with a strong base to produce the corresponding carbanion and then contacting the carbanion with a suitable halomethylating agent. The strong base must be non-nucleophilic and be of sufficient strenght to remove a proton from the methine moiety adjacent to the carboxy group of the starting ester. Suitable such bases are known in the art. Examples are: (a) an alkyl lithium (e.g. n-butyllithium), (b) an aryl lithium (e.g. phenyllithium), (c) a lithium dialkylamide (e.g. lithium diisopropylamide), (d) sodium or lithium amide, (e) a metal hydride (e.g. sodium or potassium hydride), (f) metal alcoholate (e.g. sodium or potassium tert-butoxide), or (g) lithium or dilithium acetylide. The reaction between the diester and the base can be performed in an aprotic organic solvent (such as tetrahydrofuran (THF), diethyl ether, dimethylformamide (DMF), dimethyl sulfoxide (DMSO), dimethoxyethane, or dioxane, or mixtures thereof), using a temperature range of about 0° to 70° C., preferably room temperature, and a reaction time of about 5 minutes to 2 hours. Preferred bases for forming the carbanion are sodium hydride in dimethoxyethane, potassium tert-butoxide/n-butyllithium in THF, or sodium tert-butoxide in THF.

Suitable halomethylating agents are the polyhalomethanes of the formula: $CH_2FX_a$, $CHF(X_a)_2$, $CF_2(X_a)_2$, $CH_2ClX_a$, $CHCl(X_a)_2$, $CCl_2(X_b)_2$, $CH_2BrX_b$, $CHBr(X_b)_2$, $CBr_2I_2$, or $CH_2I_2$, wherein $X_a$ is chlorine, bromine, or iodine and $X_b$ is bromine or iodine. The selection of a particular polyhalomethane to be employed for the introduction of the halomethyl group desired in the compounds of Formula (2) will be apparent to those skilled in the art. Preferred polyhalomethanes are: $CHClF_2$ and $CHBrF_2$ for introducing the —CHF$_2$ group; CHCl$_2$F for introducing the —CHClF group; —CHBrCl$_2$, and CHCl$_3$ for introducing the —CHCl$_2$ group; —CH$_2$BrCl for introducing the —CH$_2$Cl group; CHBr$_2$Cl for introducing the —CHBr$_2$ group; CHClBr for introducing the —CHBr group; CHBr$_3$ for introducing the —CHBr$_2$ group; and CBr$_2$F$_2$ for introducing the —CBrF$_2$ group.

The halomethylation of the carbanion can be carried out in situ by adding the appropriate polyhalomethane at a temperature range of about 0° to 70° C. and allowing the reaction to proceed for about 1 to 24 hours, preferably about 16 hours. Depending upon the reactivity of the reactants, the polyhalomethane can be introduced at a higher temperature (about 40° C.), and the reaction mixture can be allowed to cool to room temperature to complete the reaction or the polyhalomethane can be introduced at room temperature.

Step B is carried out in two stages. In the first stage, the halomethylmalonic acid diester of Formula (2) is cleaved by acid hydrolysis or by catalytic hydrogenation to convert either one or both of the ester groups (—COOR$_b$ or —COOR$_c$) to a free carboxylic acid group. Whether cleavage of one or both ester groups occurs will depend upon the nature of each ester group and the conditions employed for the cleavage reaction. In order to effect cleavage of only one ester group, it is preferred that the diester be mixed, the groups defined by R$_b$ and R$_c$ being chosen so that the ester group —COOR$_b$ can be selectively cleaved without cleaving the ester group —COOR$_c$. The selection of particular ester groups which can be selectively cleaved and methods for performing the selective cleavage will be apparent to those skilled in the art. To accomplish selective cleavage of the diester, it is preferred to employ a halomethyl mixed diester of Formula (2) wherein R$_b$ is tert-butyl, benzyl, diphenylmethyl, or triphenylmethyl and R$_c$ is a straight-chain C$_1$–C$_4$ alkyl group (such as methyl, ethyl, propyl, or n-butyl).

The ester group defined by —COOR$_b$ can be selectively hydrolyzed by treatment with an organic or inorganic acid, either with or without an added solvent, using a temperature range of about 0° to 25° C. and a reaction time of about 1 to 10 hours. Ambient temperature is preferred. The choice of the acid for the hydrolysis is not critical, except that the acid should be chosen so that it can be easily removed after the hydrolysis stage. Trifluoroacetic acid is preferred since its low boiling point permits it to be easily removed from the hydrolysis product. When R$_b$ is benzyl, diphenylmethyl, or triphenylmethyl and R$_c$ is a straight-chain C$_1$–C$_4$ alkyl group, the ester group —COOR$_b$ can also be selectively cleaved by subjecting the mixed diester of Formula (2) to catalytic hydrogenolysis using conventional procedures: for example, by treatment under a hydrogen atmosphere in the presence of a catalyst (e.g. Pd/C) at ambient temperature for 1 to 48 hours. As will be apparent to those skilled in the art, the ester groups can be chosen so that both groups can be cleaved simultaneously by acid hydrolysis or catalytic hydrogenolysis. Thus, when it is desired to cleave both ester groups simultaneously, each of R$_b$ and R$_c$ should be a tert-butyl, benzyl, diphenyl, or triphenylmethyl group. In the second stage of Step B the acid obtained by cleavage of the diester (either a diacid or a mixed acid-ester) is treated with a base whereby the acid undergoes decarboxylation and elimination of halide ion to afford the acrylic acid or the acrylate ester of Formula (3). Whether the product is an ester (R$_c$ is a straight-chain C$_1$–C$_4$ alkyl group) or an acid (R$_c$ is hydrogen) depends upon whether the cleavage reaction in the first stage was performed selectively or non-selectively. The reaction can be performed using an aqueous or non-aqueous solvent. Strong bases, such as sodium hydroxide and the like, or weak bases, such as triethylamine or sodium bicarbonate, can be used. However, with strong bases, care must be taken to avoid using an excess of base to avoid interaction with the double bond. Weak bases (which do not interact with the double bond) can be used in excess. The choice of a particular base, the reaction solvent, and reaction conditions will be apparent to those skilled in the art. A preferred procedure is to employ aqueous sodium hydroxide in THF at ambient temperature. In general, a temperature range of about 0° to 25° C. and reaction time of 15 minutes to 2 hours can be used.

In Step C, the acrylic acid or acrylate ester of Formula (3) is reduced to yield the allyl alcohol of Formula (4). The reducing agent employed for this transformation can be any reagent which is known in the art to be capable of selectively reducing an ester function or carboxylic acid function to the corresponding carbinol in the presence of a double bond. A preferred reducing agent is diisobutylaluminium hydride (DIBAL-H ®) in hexane, THF, diethyl ether, or dichloromethane, or mixtures thereof. In a preferred procedure, a solution of the acrylate methyl ester in THF is cooled to about 0° to −78° C. (preferably −60° to −70° C.), the DIBAL-H dissolved in hexane is added, and the temperature of the mixture is allowed to rise to ambience. The reaction time can be about 2 to 24 hours.

The allyl alcohol of Formula (4) can be converted to the desired allyl primary amine using procedures known in the art to be useful for replacing an allylic hydroxyl group by an allylic primary amino group. A preferred laboratory method is shown by Step D and Step E. This involves the direct formation of an imido derivative of Formula (6), preferably the phthalimide, and subsequent cleavage of the imido group to generate the primary amino group. In Step D, the imido derivative of Formula (6) can be prepared conveniently by treating the allyl alcohol of Formula (4) with the appropriate imide (i.e. phthalimide, succinimide, or maleimide) in the presence of a triarylphosphine (e.g. triphenylphosphine) or a trialkylphosphine and diethyl azodicarboxylate in an aprotic organic solvent (e.g. THF or dioxane). The reaction can be performed using a temperature range of about 0° to 70° C. and a reaction time of about 1 to 24 hours. Ambient temperature is preferred. In Step E, the imido derivative of Formula (6) can be cleaved, preferably by reaction with hydrazine in an organic solvent, such as an alkanol (e.g. ethanol), at reflux temperature (50° to 100° C.) and a reaction time of about 30 minutes to 10 hours. It is preferable to add an acid (e.g. hydrochloric acid) after the hydrazine treatment to convert the product to the acid addition salt. Other reagents can be used to cleave the imido function. For example, the imide can be heated with a strong mineral acid (e.g. hydrochloric or sulfuric acid) or a mixture of hydrochloric and acetic acid. Acids, such as hydrobromic acid, which are reactive towards olefins usually cannot be used. The final products of Formula (8) are conveniently purified and isolated as the acid addition salt using conventional purification methods.

The allyl alcohol of Formula (4) can also be converted to the allyl primary amine via formation (Step F) of the reactive intermediate of Formula (5), in which the —OH group is replaced by a leaving group (Q). Suitable leaving groups are known in the art. For example, chlorine, bromine, iodine, tosyloxy, or mesyloxy can be employed. Methods for replacing the hydroxy group by the leaving group are known in the art. For example, the allyl alcohol of Formula (4) can be treated with a phosphorus trihalide (e.g. $PCl_3$ or $PBr_3$) in an organic solvent, such as toluene or benzene, to introduce halogen (e.g. chlorine or bromine). The allyl alcohol can also be treated with a tosyl halide or mesyl halide (e.g. tosyl chloride or mesyl chloride) in the presence of a base (e.g. pyridine) to introduce the tosyloxy or mesyloxy group. The reactive intermediate of Formula (5) can be converted to the allyl primary amine of Formula (8) in known manner by displacement of the leaving group (Q) either in Step J directly by ammonia or in Step G by a nucleophilic group (B) which can then be cleaved (Step H) to generate the primary amino group. Examples of groups defined by B in Formula (7) which can be used to generate a primary amino group are the hexamethylenetetrammonium group, an imido group (e.g. phthalimido, succinimido, or maleimido group) or an alkylcarboxyamino group of the formula:

—NHCO$_2$R$_e$ wherein R$_e$ is (C$_1$–C$_4$)alkyl. The hexamethylenetetrammonium group can be introduced by treating the reactive intermediate of Formula (5) with hexamethylenetetramine in an organic solvent (e.g. a C$_1$–C$_4$alkanol or chloroform) using ambient temperature and a reaction time of about 30 minutes to 24 hours. The hexamethylenetetrammonium group can be cleaved to generate the primary amino group by treatment with an aqueous acid (e.g. hydrochloric acid) under reflux. Acids which are reactive to the double bond cannot be used. The imido group can be introduced by treating the reactive intermediate of Formula (5) with the appropriate alkali metal imide (e.g. sodium or potassium phthalimide, succinimide, or maleimide) in an organic solvent, such as THF, DMF, DMSO, or dioxane using a temperature range of about 0° to 70° C., preferably ambient temperature, and a reaction time of about 30 minutes to 12 hours, preferably 3 hours. The imido group can be cleaved to generate the primary amino group using the methods described supra with respect to Step E of Scheme I. The alkylcarboxyamino group (—NCHO$_2$R$_e$) can be introduced by treating the reactive intermediate of formula (7) with an alkali metal cyanate (e.g. sodium or potassium cyanate) and a C$_1$–C$_4$alkanol using a temperature range of about 70° to 150° C., preferably 100° C., and a reaction time of about 1 to 6 hours, preferably 2 hours. The alkylcarboxyamino group can be cleaved to generate the primary amino group by treatment with iodotrimethylsilane followed by hydrolysis. The reaction with iodotrimethylsilane is performed in an organic solvent (e.g. chloroform) using a temperature range of about 0° to 100° C., preferably 50° C., and a reaction time of about 1 to 24 hours, preferably 1 to 2 hours.

It should be observed that in Step B of the method depicted in Scheme I, when Z is a dihalomethyl group, elimination of the halide ion gives the geometric isomer in which the remaining halogen located on the double bond is oriented cis to the group represented by R$_a$ [i.e. the product is a compound of Formula (3) wherein X is fluorine, chlorine, or bromine and Y is hydrogen]

The compounds of Formula I or II wherein X and Y, independently, are hydrogen, chlorine, or bromine can be made by the process depicted in the DRAWINGS in Scheme II. In Scheme II the symbols R$_a$, W, and X$_d$ have the following meanings:

R$_a$ is the group R- or RA- wherein R- and RA- have the meanings set forth with respect to Formula I and Formula II, respectively, W is

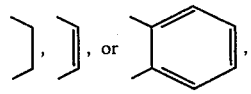

and

X$_d$ is chlorine or bromine.

In Step K, an allyl imido derivative of Formula (9) is chlorinated or brominated, using procedures known in the art to be useful for adding chlorine or bromine to a double bond. The product formed is the dihalo imido derivative of Formula (10). The bromination or chlorination reaction can be performed by treating the allyl imido derivative with chlorine or bromine in a suitable solvent, such as carbon tetrachloride, chloroform, or methylene chloride, in the absence of light using a temperature range of about −10° C. to ambient temperature, preferably 0° to 5° C., and a reaction time of about 1 to 6 hours, preferably 3 hours. The olefinic amido compounds of Formula 11a and 11b are prepared from the dihalo imido derivative by treatment with a conventional dehydrohalogenating agent. A preferred dehydrohalogenating agent is 1,5-diazabicyclo[5.4.0]undec-5-ene (DBU). The reaction is carried out in DMSO using a temperature range of from ambiance to 120° C., preferably 85°–95° C., and a reaction time of about 4 to 24 hours. The product of the dihydrohalogenation reaction is a mixture of the monochloro or monobromo allyl imido derivatives shown in Formula 11a and 11b, which compounds are isomeric and differ with respect to the orientation of the halogen atom of the double bond. The isomers can be separated by conventional methods, such as column chromatography. The individual imido derivatives of Formula 11a and 11b, or a mixture thereof, can be cleaved in Step M in known manner using the methods described supra with respect to Step E in Scheme I to yield the monohalo allyl primary amines shown in Formula (12a) or Formula (12b). The dihalo allyl primary amines of Formula (15) can be prepared in Steps N, O, and P by chlorinating or brominating the double bond of a monohalo allyl imido derivative of Formula (11a) or (11b), or a mixture thereof, to form the trihaloallyl imido derivative of Formula (13), and treating the trihalo derivative with a dehydrohalogenating reagent, and cleaving the imido function. Methods for chlorinating or brominating the double bond (Step N) and for the dehydrohalogenation reaction (Step O) are described supra with respect to Steps K and L, respectively. In Step P, the imido moiety of the dihalo allyl imido derivative of Formula (14) is cleaved to give the dihalo allyl primary amine of Formula (15) using known methods as described supra with respect to Step E of Scheme I.

The compounds of Formula I or II wherein X is hydrogen and Y is fluorine, chlorine, or bromine can be prepared from an appropriate imido derivative of Formula (6) in Scheme I, wherein Y is fluorine, chlorine, or bromine and X is hydrogen, by a process which includes halogenation of the double bond, dehalogenation to re-introduce the double bond, and cleavage of the imido function to generate the primary amine. For example, (E)-1-fluoro-2-phenyl-3-phthalimidopropene is brominated in methylene chloride in the absence of light, the 1,2-dibromo product is then debrominated using potassium iodide in acetone, and finally the phthalimido group is cleaved using hydrazine in ethanol. The major product is (Z)-2-phenyl-3-fluoroallylamine.

In the procedures of Scheme I and II, the product is the primary allylamine. The secondary allyl amines of Formula I or II can be made by conventional N-alkylation methods. For example, the N-ethyl derivatives can be made by treating the primary amine with benzaldehyde in a lower alcohol (e.g. ethanol) to form the Schiff base, treating the Schiff base with triethyloxonium tetrafluoroborate, and hydrolyzing the intermediate thus formed.

The compounds of Formula I or II, wherein R is a mono-, di-, or tri-hydroxyphenyl group, can be prepared using as the starting compound in Scheme I or II a compound wherein $R_a$ is R, wherein R is a mono-, di-, or tri-alkoxy phenyl group. The processes depicted in Scheme I or Scheme II can e carried out unchanged up to the preparation of the allyl imido derivative of Formula (6), (11a and b), or (14). At this point, the aromatic alkoxy group is cleaved to the hydroxy group using conventional ether-cleavage methods (for example, by treatment with boron tribromide). The imide function is then cleaved, as discussed supra, to generate the primary amino group.

The malonic acid diester of Formula (1) used as the starting compounds in the process depicted in Scheme I are either known compounds or they can be prepared from known compounds using known methods or obvious modifications thereof. In particular, the diester of Formula (1) can be made by acylating or appropriate carboxylic acid ester of Formula (16a) or (16b), shown below:

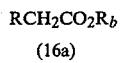  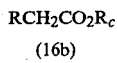

(16a)  (16b)

In Formula (16a) or (16b), $R_b$ is tert-butyl, benzyl, diphenylmethyl, or triphenyl and $R_c$ is $C_1$-$C_4$(straight-chain)alkyl, tert-butyl, benzyl, diphenylmethyl, or triphenylmethyl. Methods of acylating the ester of Formula (16a) or (16b) are known in the art. One method is to treat the ester with a non-nucleophilic strong base to produce the carbanion, and then to treat the carbonion with a suitable acylating agent. Suitable strong bases are known in the art, and are discussed with respect to Step A of Scheme I. A preferred base is lithium diisopropylamide. Any conventional acylating agent can be employed. A preferred acylating agent is a reactive halide of a formic acid alkyl ester, as shown in Formula (17a) or (17b):

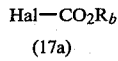  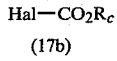

(17a)  (17b)

wherein $R_b$ and $R_c$ are as defined supra with respect to Formula (16a) or (16b) and Hal is chlorine or bromine. In a preferred acylation procedure, an ester of Formula (16a) or (16b) is treated with a base (e.g. lithium diisopropylamide) in an organic solvent (e.g. THF, dimethyl ether, acetonitrile, DMF, DMSO, or dioxane) at a low temperature (e.g. about $-30°$ to $-78°$ C., preferably $-65°$ to $-78°$ C.). The reaction can be allowed to proceed for a period of from 5 minutes to 2 hours, preferably about 1 hour. The acylation reaction can be performed by adding the haloformate ester to the cooled reaction mixture containing the carbanion and allowing the mixture to warm to room temperature. The acylation is allowed to continue for a period of about 4 to 24 hours, preferably 16 hours.

The diester of Formula (1) in Scheme I, wherein $R_a$ is RA-, as defined with respect to Formula II supra, can be made by an alternative method. In this method, a malonic acid diester of Formula (18):

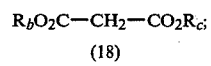

(18)

wherein $R_b$ and $R_c$ have the meanings given with respect to Formula (17a) and (17b), supra, is alkylated using an alkylating agent of Formula (19):

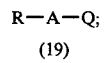

(19)

wherein RA- has the meaning given with respect to Formula II, supra, and Q is a leaving group, such as chlorine, bromine, iodine, tosyloxy, or mesyloxy. The alkylation is performed in two stages, the first being treatment with a strong base to form the carbanion, and the second being treatment of the carbanion with the alkylating agent. Methods for carrying out the malonic acid ester alkylation are discussed supra and are well known in the art.

In the compounds of Formula II and IV, the group "A" is defined as a divalent radical which is a "bridging" group inserted between the double bond and the group defined by "R". It will be apparent to those skilled in the art that the divalent radical defined by "A" can be either symetrical or unsymetrical depending upon the particular radical employed. When "A" is an unsymetrical divalent radical, it will be understood that the divalent radical must be attached to the double bond by means of the terminal carbon shown on the left side of the divalent formula as written herein, and the divalent radical must be attached to the group defined by "R" by means of the terminal carbon shown on the right side of the divalent formula as written herein.

The following examples (1 to 27) further illustrate the manner and processes for making the compounds of Formula I or II. In the examples, all temperatures are in degree Centigrade.

EXAMPLE 1

Ethyl 2-carbo-tert-butoxy(3',4'-dimethoxy)phenylacetate

A solution of lithium diisopropylamide in THF is prepared at 5° by the addition of n-butyllithium (200 ml, 1.4 M) to diisopropylamine (41.2 ml) in THF (500 ml). The temperature is lowered to about $-65°$ and a solution of tert-butyl 3,4-dimethoxyphenylacetate (65 g) in THF (100 ml) is added. After 1 hour at this temperature, the reaction mixture is treated with a solution of ethyl chloroformate (33.02 g) in THF (100 ml). Cooling is removed, and the solution is stirred overnight at room temperature. The solvent is evaporated, and the residue mixed with ether, is washed consecutively with N HCl, water, and brine. The ether solution is dried and the solvent removed by evaporation. The product (91.86 g, yellowish oil) is purified by chromatography on silica gel (1 kg) using as eluant 20% ether/80% light petroleum to give ethyl 2-carbo-tert-butoxy(3′,4′-dimethoxy)phenyl acetate (61.79 g).

NMR (CCl$_4$): δ 1.25, t (J=7 Hz), 3H; 1.43, s, 9H; 3.75, 3.78, two s, 6H; 4.12, q (J=7 Hz), 2H; 4.25, s, 1H; 6.72, s, 2H; 6.85, s, 1H.

Analysis for C$_{17}$H$_{24}$O$_6$ Found: C, 62.96; H, 7.26% Requires: C, 62.95; H, 7.46%

EXAMPLE 2

Ethyl 2-carbo-tert-butoxy(4′-methoxy)phenylacetate

A solution of lithium diisopropylamide in THF (500 ml) is prepared at 5° by the addition of n-butyllithium (427 ml of 1.5 M solution) to diisopropylamine (89.5 ml; 64.64 g) in THF (500 ml). The temperature is lowered to about −65°, and a solution of tert-butyl 4-methoxyphenylacetate (70.47 g) in THF (100 ml) is added over about 5 minutes. After 1 hour at this temperature, the reaction mixture is treated with a solution of ethyl chloroformate (34.6 g) in THF (100 ml). Cooling is removed, and the solution is stirred overnight at room temperature. 6N HCl (53 ml) is added slowly so that the temperature does not rise above 20°. The THF is evaporated, and the residue, dissolved in ether, is washed consecutatively with water, 1N HCl, and water (×4). The ether solution is dried, and the solvent is removed by evaporation to give ethyl 2-carbo-tert-butoxy(4′-methoxy)phenylacetate (93.76 g): orange oil; b.p. 124°–125°/0.05 mm:

NMR (CDCl$_3$): δ 1.17, t (J=7 Hz), 3H; 1.38, s, 9H; 3.67, s, 3H; 4.10, q (J=7 Hz), 2H; 4.37, s, 1H; centred at 6.96, A$_2$B$_2$ (J$_{AB}$=9 Hz), 4H.

EXAMPLE 3

Repeating the procedure of Example 1, but using the appropriate starting materials in place of tert-butyl 3,4-dimethoxyphenylacetate the following compounds are obtained: (a) Ethyl 2-carbo-tert-butoxyphenylacetate: b.p. 90°/0.06 mm;

NMR (CCl$_4$): δ 1.22, t (J=7 Hz), 3H; 1.38, s, 9H; 4.07, q (J=7 Hz), 2H; 4.32, s, 1H; 7.22; s, 5H.

(b) Ethyl 2-carbo-tert-butoxy(3′-methoxy)phenylacetate: b.p. 132°–133°/0.04 mm;

NMR (CCl$_4$): δ 1.20, t (J=7 Hz), 3H; 1.37, s, 9H; 3.70, s, 3H; 4.07, q (J=7 Hz), 2H; 4.23, s, 1H; 6.52 to 7.20, m, 4H.

(c) Ethyl 2-carbo-tert-butoxyphenylpropionate: b.p. 95°/0.05 mm (oven);

NMR (CDCl$_3$): δ1.20, t (J=7 Hz), 3H; 1.40, s, 9H; 3.17 and 3.55, AB$_2$ system, 3H; 4.17, q (J=7 Hz), 2H; 7.22, s, 5H.

EXAMPLE 4

Repeating the procedure of Example 2, but using the appropriate starting materials in plce of tert-butyl 4-methoxyphenylacetate, the following compounds are obtained:

(a) Ethyl 2-carbo-tert-butoxy(2′-methoxy)phenylacetate:

NMR (CCl$_4$): δ1.23, t (J=7 Hz), 3H; 1.45, s, 9H; 3.77, s, 3H; 4.13, q (J=7 Hz), 2H; 4.87, s, 1H; 6.67 to 7.43, m, 4H.

Analysis for C$_{16}$H$_{22}$O$_5$: Found: C, 65.04; H, 7.26% Requires: C, 65.29; H, 7.53%

(b) Ethyl 2-carbo-tert-butoxy(4′-chloro)phenylacetate: m.p. 56°–57°;

NMR (CDCl$_3$): δ1.27, t (J=7 Hz), 3H; 1.47, s, 9H; 4.19, q (J=7 Hz), 2H; 4.52, s, 1H; 7.35, s, 1H.

Analysis for C$_{15}$H$_{19}$ClO$_4$: Found: C, 60.32; H, 6.28% Requires: C, 60.30; H, 6.41%

(c) Ethyl 2-carbo-tert-butoxy(3′-trifluoromethyl)phenylacetate:

NMR (CCl$_4$); δ1.23, t (J=7 Hz), 3H; 1.43, s, 9H; 4.13, q (J=7 Hz), 2H; 4.43, s, 1H; 7.37 to 7.70, m, 4H.

Analysis for C$_{16}$H$_{19}$F$_3$O$_4$: Found: C, 57.97; H, 5.69% Requires: C, 57.83; H, 5.76%

(d) Ethyl 2-carbo-tert-butoxy(4′-methoxy)phenylpropionate:

NMR (CDCl$_3$): δ1.20, t (J=7 Hz), 3H; 1.38, s, 9H; 3.12 and 3.50, AB$_2$ system, 3H; 3.75, s, 3H; 4.15, q (J=7 Hz), 2H; centred at 6.97, A$_2$B$_2$ system (J=9 Hz), 4H.

Analysis for C$_{17}$H$_{24}$O$_5$: Found: C, 66.34; H, 7.94% Requires: C, 66.21; H, 7.84%

EXAMPLE 5

Ethyl 2-difluoromethyl-2-carbo-tert-butoxy(3′,4′-dimethoxy)-phenylacetate

A solution of ethyl 2-carbo-tert-butoxy(3′,4′-dimethoxy)phenylacetate (9.72 g) in dimethoxyethane (DME, 80 ml) is added to sodium hydride (1.58 g as a 50-55% dispersion in oil which was previously washed free of oil with light petroleum). When anion formation is complete the reaction mixture is heated to about 40° and a stream of chlorodifluoromethane (Freon 22) is bubbled through the mixture for a few minutes. A balloon is attached to the reaction vessel and the Freon 22 is added until the balloon is full. The heating bath is then removed and the mixture is stirred for about 16 hours. The DME is partially evaporated, and the residue is mixed with water and extracted with ether. The ether solution is washed with brine and dried (MgSO$_4$). Evaporation of the solvent gives crude ethyl 2-difluoromethyl-2-carbo-tert-butoxy(3′,4′-dimethoxy)phenylacetate (9.93 g): pale-orange oil;

NMR (CCl$_4$): δ1.25, t (J=7 Hz), 3H; 1.42, s, 9H; 3.73, s, 6H; 4.20, q (J=7 Hz), 2H; 6.25, t (J=56 Hz), 1H; 6.68, s, 2H; 6.78, s (broad), 1H.

EXAMPLE 6

Repeating the procedure of Example 5 but substituting the appropriate starting material in place of ethyl 2-carbo-tert-butoxy(3′,4′-dimethoxy)phenylacetate, the following compounds are obtained.

(a) Ethyl 2-difluoromethyl-2-carbo-tert-butoxyphenylacetate:

NMR (CCl$_4$): δ1.27, t (J=7 Hz), 3H; 1.47, s, 9H; 4.18, q (J=7 Hz), 2H; 6.30, t (J=55 Hz), 1H; 7.30, s, 5H.

Analysis for C$_{16}$H$_{20}$F$_2$O$_4$: Found: C, 61.49; H, 6.48% Requires: C, 61.14; H, 6.41%

(b) Ethyl 2-difluoromethyl-2-carbo-tert-butoxy(4′-methoxy)phenylacetate: b.p. 118°–119°/0.05 mm;

NMR (CDCl$_3$): δ1.23, t (J=7 Hz), 3H; 1.42, s, 9H; 3.67, s, 3H; 4.20, q (J=7 Hz), 2H; 6.30, t (J=57 Hz); 1H; centred at 6.97, A$_2$B$_2$ (J$_{AB}$=9 Hz), 4H.

(c) Ethyl 2-difluoromethyl-2-carbo-tert-butoxy(3′-methoxy)phenylacetate: b.p. 101°–108°/0.05 mm;

NMR (CDCl$_3$): δ1.16, t (J=7 Hz), 3H; 1.37, s, 9H; 3.63, s, 3H; 4.05, q (J=7 Hz), 2H; 6.38, t (J=54 Hz), 1H; 6.63 to 7.28, m, 4H.

Analysis for $C_{17}H_{22}F_2O_5$: Found: C, 59.16; H, 6.41% Requires: C, 59.29; H, 6.44%

(d) Ethyl 2-difluoromethyl-2-carbo-tert-butoxy(4'-chloro)phenylacetate:

NMR (CCl$_4$): δ1.28, t (J=7 Hz), 3H; 1.48, s, 9H; 4.27, q (J=7 Hz), 2H; 6.38, t(J=55 Hz), 1H; 7.28, s, 4H.

(e) Ethyl 2-difluoromethyl-2-carbo-tert-butoxyphenylpropionate:

NMR (CDCl$_3$): 1.25, t (J=7 Hz), 3H; 1.43, s, 9H; 3.38, s, 2H; 4.20, q (J=7 Hz), 2H; 6.03, t (J=55 Hz), 1H; 7.23, s, 5H.

Analysis for $C_{17}H_{22}F_2O_4$: Found: C, 62.56; H, 6.80% Requires: C, 62.18; H, 6.75%

EXAMPLE 7

Repeating the procedure of Example 5 but substituting the appropriate starting materials in place of ethyl 2-carbo-tert-butoxy(3',4'-dimethoxy)phenylacetate, and potassium-tert-butoxide/n-butyllithium in THF in place of sodium hydride in DME, the following compounds are obtained:

(a) Ethyl 2-difluoromethyl-2-carbo-tert-butoxy(2'-methoxy)phenylacetate:

NMR (CCl$_4$): δ1.25, t (J=7 Hz), 3H; 1.47, s, 9H; 3.73, s, 3H; 4.22, q (J=7 Hz), 2H; 6.53, t (J=56 Hz), 1H; 6.67 to 7.50, m, 4H.

Analysis for $C_{17}H_{22}F_2O_5$:

Found: C, 59.24; H, 6.45% Requires: C, 59.29; H, 6.44%

(b) Ethyl 2-fluoromethyl-2-carbo-tert-butoxy(3'-trifluoromethyl)phenylacetate:

NMR (CCl$_4$): δ1.30, t (J=7 Hz), 3H; 1.50, s, 9H; 4.35, q (J=7 Hz), 2H; 4.87, t (J=55 Hz), 1H; 7.60, m, 4H.

(c) Ethyl 2-difluoromethyl-2-carbo-tert-butoxy(4'-methoxy)phenylpropionate:

NMR (CDCl$_3$): δ1.25, t (J=7 Hz), 3H; 1.42, s, 9H; 3.33, s, 2H; 3.73, s, 3H; 4.18, q (J=7 Hz), 2H; 6.00, t (J=54 Hz), 1H; centred at 6.92, A$_2$B$_2$ (J$_{AB}$=9 Hz), 4H.

Analysis for $C_{18}H_{24}F_2O_5$: Found: C, 60.43, H, 5.71% Requires: C, 60.32; H, 6.75%

EXAMPLE 8

Ethyl (E)-2-(3',4'-dimethoxy)phenyl-3-fluoroacrylate

A solution of ethyl 2-difluoromethyl-2-carbo-tert-butoxy(3',4'-dimethoxy)phenylacetate (61.70 g) in trifluoroacetic acid (152 ml) is stirred at room temperature for 1 hour whereupon the mixture is evaporated to dryness. The residue is dissolved in tetrahydrofuran (THF, 70 ml) and treated with aqueous sodium hydroxide (2M, 83 ml) at room temperature for 15 minutes. The reaction mixture is diluted with water and extracted with ether. The ether solution is washed with brine, dried (MgSO$_4$), and evaporated to yield an orange oil (44.05 g). Chromatography on silica gel (200 g) using 20% ethyl acetate in light petroleum as eluant affords an oil (39.70 g) which slowly crystallizes. Purification by recrystallization from n-pentane gives ethyl (E)-2-(3',4'-dimethoxy)phenyl-3-fluoroacrylate: colorless plates; m.p. 71°–72°.

NMR (CCl$_4$): δ1.27, t (J=7 Hz), 3H; 3.75, s, 6H; 4.15, q (J=7 Hz), 2H; 6.72, s, 3H; 7.53, d (J=42 Hz), 1H.

Analysis for $C_{13}H_{15}FO_4$: Found: C, 61.49; H, 5.94% Requires: C, 61.41; H, 5.95%

EXAMPLE 9

Repeating the procedure of Example 8 but substituting the appropriate starting materials for 2-difluoromethyl-2-carbo-tert-butoxy(3',4'-dimethoxy)phenylacetate, the following compounds are obtained:

(a) Ethyl (E)-2-phenyl-3-fluoroacrylate: b.p. 81°/0.4 mm;

NMR (CCl$_4$): δ1.25, t (J=7 Hz), 3H; 4.18, q (J=7 Hz), 2H; 7.27, s, 5H; 7.80, d (J=81 Hz), 1H.

(b) Ethyl (E)-2-(3'-methoxy)phenyl-3-fluoroacrylate: b.p. 74°–75°/0.05 mm;

NMR (CDCl$_3$): δ1.35, t (J=7 Hz), 3H; 3.80, s, 3H; 4.25, q (J=7 Hz), 2H; 6.77 to 7.47, m, 4H; 7.72, d (J=82 Hz), 1H.

Analysis for $C_{12}H_{13}FO_3$: Found: C, 63.93; H, 5.89% Requires: C, 64.28; H, 5.84%

(c) Ethyl (E)-2-(2'-methoxy)phenyl-3-fluoroacrylate: b.p. 88°/0.05 mm;

NMR (CCl$_4$): δ1.20, t (J=7 Hz), 3H; 3.72, s, 3H; 4.13, q (J=7 Hz), 2H; 6.67 to 7.42, m, 4H; 7.57, d (J=82 Hz), 1H.

Analysis for $C_{12}H_{13}FO_3$: Found: C, 64.45; H, 5.82% Requires: C, 64.28; H, 5.84%

(d) Ethyl (E)-2-(3'-trifluoromethyl)phenyl-3-fluoroacrylate;

NMR (CDCl$_3$): δ1.30, t (J=7 Hz), 3H; 4.28, q (J=7 Hz), 2H; 7.55, m, 4H; 7.80, d (J=80 Hz), 1H.

(e) Ethyl (E)-2-(4'-chloro)phenyl-3-fluoroacrylate;

NMR (CCl$_4$): δ1.27, t(J=7 Hz), 3H; 4.22, q(J=7 Hz), 2H; 7.27, s, 4H; 7.67, d (J=81 Hz), 1H.

(f) Ethyl (E)-2-(4'-methoxy)benzyl-3-fluoroacrylate: b.p. 104°/0.04 mm;

NMR (CDCl$_3$): δ1.18, t (J=7 Hz), 3H; 3.53, d (J=3 Hz), 2H; 3.70, s, 3H; 4.12, q (J=7 Hz), 2H; centred at 6.93, A$_2$B$_2$ (J$_{AB}$=9 Hz), 4H; 7.55, d (J=83 Hz), 1H.

Analysis for $C_{13}H_{15}FO_3$:

Found: C, 65.50; H, 6.49% Requires: C, 65.53; H, 6.34%

(g) Ethyl (E)-2-benzyl-3-fluoroacrylate: b.p. 75° (oven/0.05 mm;

NMR (CDCl$_3$): δ1.18, t (J=7 Hz), 3H; 3.60, d (J=3 Hz), 2H; 4.12, q (J=7 Hz), 2H; 7.18, s, 5H; 7.60, d (J=83 Hz), 1H.

(h) Ethyl (E)-2-(4'-methoxy)phenyl-3-fluoroacrylate: b.p. 89°–90°/0.04 mm;

NMR (CDCl$_3$): δ1.42, t (J=7 Hz), 3H; 3.90, s, 3H; 4.37, q (J=7 Hz), 2H; centred at 7.17, A$_2$B$_2$ (J$_{AB}$=9 Hz), 4H; 7.77, d (J=80 Hz), 1H.

Analysis for $C_{12}H_{13}FO_3$: Found: C, 63.80; H, 5.835 Requires: C, 64.28; H, 5.84%

EXAMPLE 10

(E)-2-(3',4'-Dimethoxy)phenyl-3-fluoroallyl alcohol

A solution of ethyl (E)-2-(3',4'-dimethoxy)-3-fluorofluoroacrylate (35 g) in THF (650 ml) is cooled to about −78° and treated with a solution of diisobutylaluminium hydride (690 ml) in hexane (1 M solution). The cooling bath is removed and the temperature is allowed to rise to room temperature over about 4½ hours. The solution is again cooled (ca 5°) and is then cautiously treated with methanol (140 ml) followed by 10% aqueous KOH (70 ml). The mixture is dried by the addition of MgSO$_4$ and filtered. The solids are washed thoroughly with methanol. Solvent is removed by evaporation to leave an almost colorless, crystalline mass (25.48 g). Usually, this product is used directly in the next reaction step without purification. If necessary, the product can be recrystallized from n-hexane which gives (E)-2-(3',4'-dimethoxy)phenyl-3-fluoroallyl alcohol: colorless plates; m.p. 56°–57°;

NMR (CDCl$_3$): δ2.60, s (broad), 1H; 3.83, s, 6H; 4.25, d (J=5 Hz), 2H; 6.78, d (J=83 Hz), 1H; 6.68 to 7.20, m, 3H.

Analysis for C$_{11}$H$_{13}$FO$_3$:

Found: C, 62.21; H, 6.32% Requires: C, 62.26; H, 6.17%

EXAMPLE 11

Repeating the procedure of Example 10 but substituting the appropriate starting materials for ethyl (E)-2-(3,4-dimethoxy)phenyl-3-fluoroacrylate, the following compounds are obtained:

(a) (E)-2-Phenyl-3-fluoroallyl alcohol:

NMR (CDCl$_3$): δ1.68, s, 1H; 4.33, d (broadened, J=5 Hz), 2H; 6.17, s, ½H; 7.20 to 7.63, m, 5½H.

(b) (E)-2-(3'-Methoxy)phenyl-3-fluoroallyl alcohol: m.p. 47°-48°;

NMR (CDCl$_3$): δ2.13, s, 1H; 3.85, s, 3H; 4.37, m, 2H; 6.92, d (broad, J=82 Hz); 1H, 7.13 to 7.53, m, 4H.

(c) (E)-2-(2'-Methoxy)phenyl-3-fluoroallyl alcohol:

NMR (CCl$_4$): δ3.27, s, 1H; 3.67, s, 3H; 4.08, d.d (J=5 Hz, 1.5 Hz), 2H; 6.60 to 7.40, m, 4H; 6.45, d (J=82 Hz), 1H.

(d) (E)-2-(3'-Trifluoromethyl)phenyl-3-fluoroallyl alcohol.

(e) (E)-2-(4'-Chloro)phenyl-3-fluoroallyl alcohol.

(f) (E)-2-(4'-Methoxy)benzyl-3-fluoroallyl alcohol:

NMR (CDCl$_3$): δ2.48, s (broad), 1H; 3.30, d (J=2 Hz), 2H; 3.60, s, 3H; 3.70, d (J=4 Hz), 2H; 6.52, d (J=84 Hz), 1H; centred at 6.82, A$_2$B$_2$ (J$_{AB}$=9 Hz), 4H.

(g) (E)-2-Benzyl-3-fluoroallyl alcohol:

NMR (CCl$_4$): δ3.43, m, 3H, 3.72, d (broad, J=4 Hz), 2H; 6.53, d (J=85 Hz), 1H; 7.17, m, 5H.

(h) (E)-2-(4'-Methoxy)phenyl-3-fluoroallyl alcohol; m.p. 43°-44°:

NMR (CDCl$_3$): δ1.93, s, 1H; 3.80, s, 3H; 4.33, d (broad, J=4.5 Hz), 2H; 6.82, d (J=82 Hz), 1H; centred at 7.20, A$_2$B$_2$ (J$_{AB}$=9 Hz).

EXAMPLE 12

(E)-1-Fluoro-2-(3',4'-dimethoxy)phenyl-3-phthalimidopropene

A solution of (E)-2-(3',4'-dimethoxy)phenyl-3-fluoroallyl alcohol (25 g), triphenylphosphine (31.23 g), and phthalimide (17.52 g) in THF (450 ml) is treated with a solution of diethyl azodicarboxylate (20.74 g) in THF (100 ml). The mixture is then stirred for about 16 hours. The THF is evaporated, and the by-products are largely removed by recrystallization from toluene, and then from ether. The solvent is evaporated, and the residue is purified by chromatography on silica gel (1 kg) using 20% ethyl acetate in light petroleum. The major fraction (20.48 g) is recrystallized from dichloromethane/n-hexane to give 1-fluoro-2-(3',4'-dimethoxy)phenyl-3-phthalimidopropene (16.50 g): colorless plates; m.p. 102°-103°;

NMR (CDCl$_3$): δ3.80, 3.85, two overlapping singlets, 6H; 4.52, m, 2H; 6.32, s, ½H; 6.68 to 7.28, m, 3H; 7.52 to 7.88, m, 4½H.

Analysis for C$_{19}$H$_{16}$FNO$_4$: Found: C, 66.76; H, 4.89; N, 4.34% Requires: C, 66.86; H, 4.72; N, 4.10%

EXAMPLE 13

Repeating the procedure of Example 12 but substituting the appropriate starting materials for (E)-2-(3',4'-dimethoxy)phenyl-3-fluoroallyl alcohol, the following compounds are obtained:

(a) (E)-1-Fluoro-2-phenyl-3-phthalimidopropene: m.p. 98°-99°;

NMR (CDCl$_3$): δ4.55, m, 2H; 6.32, s (broad), ½H; 7.13 to 7.93, m, 9½H.

Analysis for C$_{17}$H$_{12}$FNO$_2$: Found: C, 72.63; H, 4.49; N, 4.47% Requires: C, 72.59; H, 4.30; N, 4.98%

(b) (E)-1-Fluoro-2-(3'-methoxy)phenyl-3-phthalimidopropene: m.p. 85°-86°;

NMR (CDCl$_3$): δ3.80, s, 3H; 4.57, m, 2H; 6.30, s (broad), ½H; 6.63 to 7.43, m, 4H; 7.50 to 7.96, m, 4½H.

(c) (E)1-Fluoro-2-(2'-methoxy)phenyl-3-phthalimidopropene: m.p. 128°-129°;

NMR (CDCl$_3$): δ3.68, s, 3H; 4.50, m, 2H; 6.20, s, ½H; 6.53 to 7.40, m, 4H; 7.60, m, 4½H.

Analysis for C$_{18}$H$_{14}$FNO$_3$: Found: C, 69.43; H, 4.69; N, 4.48%

Requires: C, 69.45; H, 4.53; N, 4.50%

(d) (E)-1-Fluoro-2-(3'-trifluoromethyl)-phenyl-3-phthalimidopropene:

NMR (CDCl$_3$): δ4.57, d (J=4 Hz, broad), 2H; 3.82, s, ½H; 4.38 to 7.83, m, 8½H.

(e) (E)-1-Fluoro-2-(4'-chloro)phenyl-3-phthalimidopropene: m.p. 118°-119°;

NMR (CDCl$_3$): δ4.50, m, 2H; 6.32, s (broad), ½H; 7.07 to 7.83, m, 8½H.

Analysis for C$_{17}$H$_{11}$ClFNO$_2$: Found: C, 64.57; H, 3.67; N, 4.32% Requires: C, 64.67; H, 3.51; N, 4.44%

(f) (E)-1-Fluoro-2-(4'-methoxy)benzyl-3-phthalimidopropene: m.p. 138°-139°;

NMR (CDCl$_3$): δ3.33, d (J=2.5 Hz), 2H; 3.58, s, 3H; 4.07, d (J=3 Hz), 2H; centred at 6.83, A$_2$B$_2$ (J$_{AB}$=9 Hz), 4H; 6.88, d (J=86 Hz), 1H; 7.68, s (braod), 4H.

(g) (E)-1-Fluoro-2-benzyl-3-phthalimidopropene: m.p. 114°-115°;

NMR (CDCl$_3$): δ3.45, d (J=2.5 Hz), 2H; 4.13, d.d (J=3 Hz, 1 Hz), 2H; 6.21, s (broad), ½H; 7.20 to 7.30, m, 5H; 7.67, m, 5½H.

Analysis for C$_{18}$H$_{14}$FNO$_2$: Found: C, 73.22; H, 5.16; N, 4.63% Requires: C, 73.21; H, 4.78; N, 4.74%

(h) (E)-1-Fluoro-2-(4'-methoxy)phenyl-3-phthalimidopropene: m.p. 169°-170°;

NMR (CDCl$_3$): δ3.78, s, 3H; 4.55, d.d (J=3.5 Hz, 1.5 Hz), 2H; 7.00, m, ½H; centred at 7.50, A$_2$B$_2$ (J$_{AB}$=9 Hz), 4H; 7.63 to 7.90, m, 4½H.

Analysis for C$_{18}$H$_{14}$FNO$_3$: Found: C, 69.42; H, 4.51; N, 4.40% Requires: C, 69.45; H, 4.53; N, 4.50%

EXAMPLE 14

(E)-2-(3',4'-Dimethoxy)phenyl-3-fluoroallylamine

A mixture of (E)-1-fluoro-2-(3',4'-dimethoxy)phenyl-3-phthalimidopropene (6.82 g) and hydrazine hydrate (1.10 g) in methanol (45 ml) is refluxed for 3 hours. To the reaction mixture is added 18% aqueous hydrochloric acid (12 ml). Refluxing is continued for another 30 minutes. The mixture is cooled and filtered. Solvent is removed by evaporation to give a residue which is triturated several times with methanol. Crystallization of the solid residue from ethanol/diethyl ether gives 2-(3',4'-dimethoxy)phenyl-3-fluoroallylamine, as the hydrochloride (2.56 g): colorless plates; m.p. 216°-217°;

NMR (D$_2$O): δ3.87, s, 6H overlapping 4.00, d (broad, J=4 Hz), 2H; 7.10, s (broad), 3H; 7.17, d (J=82 Hz), 1H.

Analysis for C$_{11}$H$_{15}$ClFNO$_2$: Found: C, 53.38; H, 6.02; N, 5.60% Requires: C, 53.34; H, 6.10; N, 5.65%

EXAMPLE 15

Repeating the procedure of Example 14, but substituting the appropriate starting materials for (E)-fluoro-2-(3',4'-dimethoxyphenyl)-3-phthalimidopropene, the following compounds are obtained:

(a) (E)-2-Phenyl-3-fluoroallylamine, as the hydrochloride: m.p. 195°-196°;
NMR (D$_2$O): δ3.98, d (J=3 Hz), 2H; 7.13, d (J=8 Hz), 1H; 7.50, s, 5H.
Analysis for C$_9$H$_{11}$ClFN: Found: C, 57.53; H, 5.93; N, 7.52% Requires: C, 57.61; H, ;b 5.91; N, 7.46%

(b) (E)-2-(3'-Methoxy)phenyl-3-fluoroallylamine, as the hydrochloride: m.p. 146°-147°;
NMR (D$_2$O): δ3.87, s, 3H; 4.00, d (J=3.5 Hz), 2H; 7.18, d (J=80 Hz), 1H; 6.91 to 7.67, m, 4H.
Analysis for C$_{10}$H$_{13}$ClFNO: Found: C, 55.25; H, 5.81; N, 6.41% Requires: C, 55.18; H, 6.02; N, 6.43%

(c) (E)-2-(2'-Methoxy)phenyl-3-fluoroallylamine, as hydrochloride: m.p. 224°-225°;
Analysis for C$_{10}$H$_{13}$ClFNO: Found: C, 55.10, H, 5.89; N, 6.41% Requires: C, 55.18; H, 6.02; N, 6.43%

(d) (E)-2-(4'-Chloro)phenyl-3-fluoroallylamine, as the hydrochloride: m.p. 190°;
NMR (CD$_3$OD): δ3.97, d (broad, J=4 Hz), 2H; 7.27, d (J=81 Hz), 1H; 7.53, s, 4H.
Analysis for C$_9$H$_{10}$Cl$_2$FN: Found: C, 48.47; H, 4.44; N, 6.26% Requires: C, 48.67; H, 4.54; N, 6.31%

(e) (E)-2-(4'-Methoxy)benzyl-3-fluoroallylamine, as the hydrochloride: m.p. 185°-186°;
Analysis for C$_{11}$H$_{15}$ClFNO: Found: C, 57.09; H, 6.49; N, 6.00% Requires: C, 57.02; H, 6.53; N, 6.05%

(f) (E)-2-2-Benzyl-3-fluoroallylamine, as the hydrochloride: m.p. 179°;
NMR (D$_2$O): δ3.50, d.d (J=3 Hz, 1 Hz), 2H, 3.63, d (J=2.5 Hz), 2H; 7.05, d.m (J=82 Hz), 1H; 7.37, s, 5H.
Analysis for C$_{10}$H$_{13}$ClFN: Found: C, 59.30; H, 6.43; N, 6.91% Requires: C, 59.56; H, 6.50; N, 6.95%

(g) (E)-2-(4'-Methoxy)phenyl-3-fluoroallyl amine, as the hydrochloride; m.p. 87°;
NMR (D$_2$O): δ3.88, s, 3H; 3.97, d (broad, J=3.5 Hz), 2H; 7.12, d (J=82 Hz), 1H; centred at 7.30, A$_2$B$_2$ (J$_{AB}$=9 Hz), 4H.
Analysis for C$_{10}$H$_{13}$ClFNO: Found: C, 54.84; H, 5.90; N, 6.24% Requires: C, 55.18; H, 6.03; N, 6.43%

EXAMPLE 16

(E)-N-Methoxycarbonyl 2-phenyl-3-fluoroallylamine

A solution of phosphorous tribromide (227 mg) in toluene (2 ml) is slowly added to a solution of (E)-2-phenyl-3-fluoroallyl alcohol (305 mg) in toluene at about −5° so that the temperature does not rise above 0°. The cooling bath is removed and stirring is continued for 3 hours. The reaction mixture is then poured into saturated, aqueous potassium carbonate (20 ml). The mixture is extracted with ether, and the ether solution is washed with water and dried (MgSO$_4$). Evaporation of solvent gives (E)-2-phenyl-3-fluoroallyl bromide (318 mg); colorless oil;
NMR (CDCl$_3$): δ4.13, d (J=4 Hz), 2H; 6.85, d (J=80 Hz), 1H; 7.10 to 7.50, m, 5H.

Without purification a portion of this bromide (185 mg) is heated at 100° for 3 hours in dimethylformamide (DMF), 5 ml) containing methanol (65 mg) and potassium cyanate (60 mg). The mixture is cooled and filtered. The filtrate is then diluted with water and extracted with ether. The ether extract is washed with water and dried (MgSO$_4$), and evaporated to give a yellowish solid (135 mg). Recrystallization from diethyl ether/light petroleum give N-methoxycarbonyl 2-phenyl-3-fluoroallylamine (123 mg): colorless needles; m.p. 73°-74°;
NMR (CDCl$_3$): δ3.49, s, 3H; 3.90, m, 2H; 5.23, s (broad), 1H; 6.00, s (broad), ½H; 7.07 to 7.50, m, 5½H.

EXAMPLE 17

Repeating the procedure of Example 16 but substituting the appropriate starting materials in place of (E)-2-phenyl-3-fluoroallyl alcohol and methyl alcohol the following compounds are obtained:

(a) (E)-N-tert-Butoxycarbonyl-2-(2'-methoxy)phenyl-3-fluoroallylamine: colorless oil;
NMR (CDCl$_3$): δ1.37, s, 9H; 3.75, s, 3H; 3.92, m, 2H; 4.80, m, 1H; 6.67 to 7.28, m, 4H; 6.73, d (J=82 Hz), 1H.
Analysis for C$_{15}$H$_{20}$FNO$_3$: Found: C, 64.03; H, 7.32; N, 4.94% Requires: C, 64.04; H, 7.16; N, 4.98%

(b) (E)-N-tert-Butoxycarbonyl-2-(4'-chloro)phenyl-3-fluoroallylamine: m.p. 50°-51°;
NMR (CDCl$_3$): δ1.42, s, 9H; 4.00, m, 2H; 4.48, m, 1H; 6.80, d (J=82 Hz), 1H; 7.38, s, 4H.
Analysis for C$_{14}$H$_{17}$CLFNO$_2$:
Found: C, 58.98; H, 6.08; N, 4.94% Requires: C, 58.85; H, 6.00; N, 4.90%

EXAMPLE 18

2-Phenylallylamine hydrochloride (A) N-Methoxycarbonyl-2-phenylallylamine

A mixture of 2-phenyl-3-bromo-1-propene (67% of the mixture) and 1-bromo-2-phenyl-1-propene (33%) was prepared by the method of S. Reed, J. Org. Chem., 30, 3258 (1965). A portion of this mixture (18 g) is dissolved in dimethylformamide (DMF, 20 ml) and treated with methanol (7.7 g) and finely-powdered, dry potassium cyanate (8.1 g) at 200° for 2 hours. The mixture is cooled and filtered. The filtrate is then diluted with water and extracted with ether. The ether extract is washed with water, and dried (MgSO$_4$). Evaporation of solvent yields an orange oil (17.5 g). Chromatography on silica gel (200 ml) using 15% ethyl acetate in light petroleum gives pure N-methoxycarbonyl 2-phenylallylamine (9.5 g): colorless oil; b.p. 103°-105° (0.005 mm);
NMR (CDCl$_3$): δ3.42, s, 3H; 4.00, d (J=6 Hz), 2H; 5.03, s (broad), 1H; 5.20, s, 1H; 5.60, t (broad), 1H; 6.92 to 7.33, m, 5H.
Analysis for C$_{11}$H$_{13}$NO$_2$: Found: C, 69.08; H, 6.88; N, 7.21% Requires: C, 69.09; H, 6.90; N, 7.24%

(B) 2-Phenylallylamine

A solution of N-methoxycarbonyl 2-phenylallylamine (0.88 g) in chloroform (2.5 ml) is treated with iodotrimethylsilane (1.20 g) at 50° for 90 minutes. The solution is cooled to room temperature. Methanol (0.64 g) is added, and, after 30 minutes, the solvents are evaporated. The resulting 2-phenylallylamine is dissolved in ether and treated with ether saturated with hydrogen chloride. 2-Phenylallylamine, as the hydrochloride (0.65 g) is formed: colorless plates, m.p. 178°-179°;
NMR (D$_2$O): δ4.07, s, 2H; 5.43, m, 1H; 5.66, s, 1H; 7.45, s, 5H.
Analysis for C$_9$H$_{12}$ClN:
Found: C, 63.72; H, 7.13; N, 8.26% Requires: C, 63.70; H, 7.12; N, 8.08%

EXAMPLE 19

2-Phenyl-3-bromoallylamine (A) 2-Phenyl-3-phthalimidopropene

A mixture of 2-phenyl-3-bromo-1-propene (75% of the mixture) and 1-bromo-2-phenyl-1-propene (25%) is prepared by the method of S. Reed, J. Org. Chem., 30, 3258 (1965).

A portion (30.13 g) of this mixture is treated with potassium phthalimide (21.20 g) in DMF (100 ml) at 90° for 3 hours. The mixture is then cooled in an ice-bath, quenched with cold water, and extracted with chloroform. The chloroform extract is washed with brine, dried ($MgSO_4$) and evaporated to yield a partially crystalline mass. Trituration with methanol followed by recrystallization from chloroform/light petroleum affords 2-phenyl-3-phthalimidopropene (18.6 g): colorless needles; m.p. 122°–124°;

NMR ($CDCl_3$): δ4.63, m, 2H; 5.00, s (broad), 1H; 5.33, s, 1H; 6.97 to 7.90, m, 9H.

2-Phenyl-3-phthalimidopropene is a known compound. See Lattrell, R. and Lohaus, G., Liebigs Ann Chem., 870 (1974);

(B) 1,2-Dibromo-2-phenyl-3-phthalimidopropene

To a stirred solution of 2-phenyl-3-phthalimidopropane (2.63 g) in carbon tetrachloride (50 ml) at about 5° in the absence of light is added dropwise a solution of bromine (1.76 g) in carbon tetrachloride (40 ml). The mixture is subsequently stirred for 3 hours, water (50 ml) is added, and the two phases are decolorized with an aliquot of aqueous sodium sulfite. Evaporation of the organic layer gives a colorless mass (4.25 g) which crystallizes from n-hexane/chloroform to give 1,2-dibromo-2-phenyl-3-phthalimidopropane (3.85 g): colorless needles; m.p. 162°–163°;

NMR ($CDCl_3$): δ4.42, q AB ($\nu_A$=4.60, $\nu_B$=4.23, J=12 Hz), 2H; 4.65, m, 2H; 7.38 to 8.17, m, 9H.

Analysis for $C_{17}H_{13}Br_2NO_2$: Found: C, 48.02; H, 3.09; N, 3.14% Requires: C, 48.26; H, 3.10; N, 3.31%

(C) 1-Bromo-2-phenyl-3-phthalimidopropene

A solution of 1,2-dibromo-2-phenyl-3-phthalimidopropane (1.27 g) and 1,8-diazabicyclo[5.4.0]undec-7-ene (DBU, 0.51 g) in dimethyl sulfoxide (DMSO, 50 ml) is heated at 90° for 16 hours. The solution is cooled, diluted with ice-water, and exhaustively extracted with ether. The orange oil (0.98 g) is chromatographed on silica gel (75 g) with 20% ethyl acetate in light petroleum as eluent to give a colorless mass which is crystallized from n-hexane/dichloromethane to give 1-bromo-2-phenyl-3-phthalimidopropene (0.66 g): colorless plates; m.p. 128°–129°;

NMR ($CDCl_3$): δ4.58, d (J=1.5 Hz), 2H; 6.48, t (J=1.5 Hz), 1H; 7.28, s, 5H; 7.53 to 7.90, m, 4H.

Analysis for $C_{17}H_{12}BrNO_2$: Found: C, 59.90; H, 3.58; N, 4.12;% Requires: C, 59.67; H, 3.53; N, 4.09%

(D) 2-Phenyl-3-bromoallylamine

A mixture of 1-bromo-2-phenyl-3-phthalimidopropene (0.34 g) and hydrazine hydrate (0.06 g) in methanol (5 ml) is refluxed for 2½ hours after which 50% aqueous hydrochloric acid (4 ml) is added. Heating is continued for another hour. The mixture is cooled and filtered. Evaporation of solvent gives a solid residue which is triturated several times with methanol. Recrystallization from ethanol/diethyl ether affords 2-phenyl-3-bromoallylamine as the hydrochloride (0.17 g): colorless needles; m.p. 190°–191°;

NMR ($D_2O$): δ4.03, s (broad), 2H; 6.93, s (broad), 1H; 7.48, s, 5H.

Analysis for $C_9H_{11}BrClN$: Found: C, 43.48; H, 4.37; N, 5.62% Requires: C, 43.49; H, 4.46; N, 5.64%

EXAMPLE 20

2-Phenyl-3,3-dibromoallylamine (A) 1,1,2-Tribromo-2-phenyl-3-phthalimidopropane Bromination of 1-bromo-2-phenyl-3-phthalimidopropene (1.03 g) using the procedure of Example 19 B gives a colorless solid (1.42 g). Recrystallization from n-hexane/dichloromethane gives 1,1,2-tribromo-2-phenyl-3-phthalimidopropane (1.22 g): colorless needles; m.p. 175°–176°;

NMR ($CDCl_3$): δ 4.67, m, 2H; 6.55, s, 1H; 7.08 to 7.83, m, 9H.

Analysis for $C_{17}H_{12}Br_3NO_2$: Found: C, 40.81; H, 2.48; N, 2.89% Requires: C, 40.67; H, 2.41; N, 2.79%

(B) 1,1-Dibromo-2-phenyl-3-phthalimidopropene

A solution of 1,1,2-tribromo-2-phenyl-3-phthalimidopropane (1.22 g) and DBU (0.50 g) in DMSO (50 ml) is heated at 85° for 4 hours. Work-up as described in Example 19 C gives 1,1-dibromo-2-phenyl-3-phthalimidopropene (0.71 g): colorless needles; m.p. 154°–155°;

NMR ($CDCl_3$): δ 4.78, s, 2H; 7.13, s, 5H; 7.65, s, 4H.

Analysis for $C_{17}H_{12}Br_2NO_2$: Found: C, 48.57; H, 2.67; N, 3.43% Requires: C, 48.45; H, 2.63; N, 3.33%

(B) 2-Phenyl-3,3-dibromoallylamine hydrochloride

Treatment of 1,1-dibromo-2-phenyl-3-phthalimidopropene (421 mg) with hydrazine hydrate (55 mg) and methanol (6 ml) followed by 50% aqueous hydrochloric acid as described in Example 19 D gives 2-phenyl-3,3-dibromoallylamine hydrochloride (175 mg): colorless needles; m.p. 243°–244°;

NMR ($CD_3OD$): δ 4.12, s (broad), 2H, 7.38, s, 5H.

Analysis for $C_9H_{12}Br_2ClN$: Found: C, 32.81; H, 3.09; N, 4.36% Requires: C, 33.02; H, 3.08; N, 4.28%

EXAMPLE 21

(Z)- and (E)-2-Phenyl-3-chloroallylamine (A) 1,2-Dichloro-2-phenyl-3-phthalimidopropane A solution of 2-phenyl-3-phthalimidopropene (7.9 g) in dichloromethane (100 ml) is cooled in an ice-bath and protected from light. Chlorine gas is then bubbled through the solution for 5 minutes. After 10 minutes, the mixture is poured into brine (200 ml). The resulting mixture is then extracted with pentane. The pentane extract is washed successively with water, 2% aqueous sodium bicarbonate, and water. The extract is dried and the solvent removed by evaporation. The resulting colorless residue (9.30 g) is crystallized from n-hexane/dichloromethane to give 1,2-dichloro-2-phenyl-3-phthalimidopropane (6.70 g): colorless needles; m.p. 114°–115°;

NMR ($CDCl_3$): δ 4.22, q AB ($\nu_A$=4.50, $\nu_B$=3.94, J=12.5 Hz), 2H; 4.32, s, 2H; 7.17 to 7.97, m, 5H.

Analysis for $C_{17}H_{13}ClNO_2$: Found: C, 61.40; H, 3.94; N, 4.18% Requires: C, 61.10; H, 3.92; N, 4.19%

(B) (Z)- and (E)-1-Chloro-2-phenyl-3-phthalimidopropene A solution of 1,2-dichloro-2-phenyl-3-phthalimidopropene (4.00 g) and DBU (2.74 g) in DMSO (200 ml) is heated at 95° for 12 hours. The reaction mixture is cooled, diluted with ice-water (300 ml), and extracted with ether. The ether solution is washed with water and dried. Evaporation of solvent affords a brown oil (3.98 g). Chromatography on silica gel (170 g), using 10% ethyl acetate in light petroleum as eluant, gives two major products. These are:

1. (E)-1-Chloro-2-phenyl-3-phthalimidopropene (0.91 g) which crystallizes from n-hexane/dichloromethane as colorless needles; m.p. 106°–108°;

NMR (CDCl$_3$): δ 4.58, d (J=1 Hz), 2H; 6.38, t (distorted), 1H; 7.30, s, 5H; 7.55 to 7.88, m, 4H.

Analysis for C$_{17}$H$_{12}$ClNO$_2$: Found: C, 68.65; H, 4.18; N, 4.48% Requires: C, 68.58; H, 4.06; N, 4.70%

2. (Z)-1-Chloro-2-phenyl-3-phthalimidopropene (0.93 g) which crystallizes from n-hexane/dichloromethane as colorless needles: m.p. 133°–134°;

NMR (CDCl$_3$): δ 4.95, d (J=1.8 Hz), 2H; 6.42, t (distorted), 1H; 7.32, s, 5H; 7.57 to 7.90, m, 4H.

Analysis for C$_{17}$H$_{12}$ClNO$_2$: Found: C, 68.86; H, 4.08; N, 4.61% Requires: C, 68.58; H, 4.06; N, 4.70%

(C) (Z)-2-Phenyl-3-chloroallylamine (Z)-1-Chloro-2-phenyl-3-phthalimidopropene (450 mg) is treated as described in Example 14 with hydrazine hydrate (85 mg) in methanol (6 ml). Hydrolysis with 50% aqueous hydrochloric acid (4 ml) and recrystallization of the product from ethanol/diethyl ether gives (Z)-2-phenyl-3-chloroallyl amine as the hydrochloride (142 mg): colorless needles; m.p. 156°–157°;

NMR (D$_2$O/DCl): δ 4.32, s, 2H; 6.75, s, 1H; 7.40, s, 5H.

Analysis for C$_9$H$_{11}$Cl$_2$N: Found: C, 53.02; H, 5.57; N, 6.83% Requires: C, 52.97; H, 5.43; N, 6.86%

(D) (E)-2-Phenyl-3-chloroallylamine (E)-1-Chloro-2-phenyl-3-phthalimidopropene (445 mg) is treated as described for the Z-isomer with hydrazine hydrate (85 mg) in methanol (6 ml). Hydrolysis with 50% aqueous hydrochloric acid gives (E)-2-phenyl-3-chloroallylamine hydrochloride (152 mg): colorless needles; m.p. 185°–186°;

NMR (D$_2$O/DCl): δ 4.07, s (broad), 2H; 6.78, m, 1H; 7.50, s, 5H.

Analysis for C$_9$H$_{11}$Cl$_2$N: Found: C, 52.86; H, 5.45; N, 6.75% Requires: C, 52.97; H, 5.43; N, 6.86%

EXAMPLE 22

(A) (E)-N-Ethyl 2-(3′-methoxy)phenyl-3-fluoroallylamine (E)-2-(3′-Methoxy)phenyl-3-fluoroallylamine hydrochloride is treated with 10% aqueous sodium hydroxide, and the mixture is extracted with ether. The ether solution is washed with water and dried. Evaporation of the solvent yields the free amine as an oil.

A mixture of (E)-2-(3′-methoxy)phenyl-3-fluoroallylamine (220 mg) and freshly-distilled benzaldehyde (150 mg) in ethanol (1 ml) is refluxed for 45 minutes. Solvent is evaporated to give a residue (315 mg) which is dissolved in dichloromethane (3 ml) and treated with triethyloxonium tetrafluoroborate (230 mg) at room temperature for about 16 hours. The solvent is evaporated and the residue is refluxed for 30 minutes with water (2 ml) and ethanol (7 ml). After evaporation of solvent, the solution is diluted with water, washed with ether and made alkaline with 10% aqueous sodium hydroxide. The alkaline solution is then extracted with ether. The ether extract is washed with water, dried, and evaporated to leave an orange oil (205 mg). This product is dissolved in ethanol and treated with a saturated solution of hydrogen chloride in ether. The resulting precipitate is crystallized from ethanol/diethyl ether to give (E)-N-ethyl 2-(3′-methoxy)phenyl-3-fluoroallylamine hydrochloride (181 mg): colorless needles; m.p. 166°–167°;

NMR (D$_2$O): δ 1.25, t (J=7.5 Hz), 3H; 3.10, q (J=7.5 Hz), 2H; 3.87, s, 3H; 4.05, d (J=3 Hz), 2H; 7.20, d (J=80 Hz), 1H; 6.93 to 7.67, m, 4H,

Analysis for C$_{12}$H$_{17}$ClFNO: Found: C, 58.79; H, 6.80; N, 5.55% Requires: C, 58.66; H, 6.97; N, 5.70%

(B)-(E)-N-Ethyl 2-(3′,4′-dimethoxy)phenyl-3-fluoroallylamine

Repeating the procedure of part (A), but substituting (E)-2-(3′,4′-dimethoxy)phenyl-3-fluoroallylamine hydrochloride for (E)-2-(3′-methoxy)phenyl-3-fluoroallylamine hydrochloride, there is obtained:

(E)-N-ethyl 2-(3′,4′-dimethoxy)phenyl-3-fluoroallylamine, as the hydrochloride: m.p. 145°;

NMR (D$_2$O): δ 1.28, t (J=8 Hz), 3H; 3.13, q (J=8 Hz), 2H; 3.90, s, 6H; 4.03, d (broad, J=3 Hz), 2H; 7.13, s (broad), 3H; 7.17, d (J=82 Hz), 1H.

Analysis for C$_{13}$H$_{19}$ClFNO$_2$: Found: C, 56.67; H, 6.97; N, 5.04% Requires: C, 56.62; H, 6.95; N, 5.08%

EXAMPLE 23

2-Phenyl-3,3-difluoroallylamine (A) Ethyl 2-bromodifluoromethyl-2-carbo-tert-butoxyphenylacetate A solution of ethyl 2-carbo-tert-butoxyphenylacetate (15.84 g, 60 mmol) in tetrahydrofuran (THF, 200 ml) is added to sodium hybride (5.76 g, ca 120 mmol, 50–55% dispersion in oil which was washed with dry light petroleum to remove the oil). When anion formation is complete, the bath temperature is raised to about 40° and a solution of dibromodifluoromethane (63 g, 300 mmol) in THF (100 ml) is added. The mixture is stirred at this temperature for 30 minutes, and then is allowed to cool to room temperature over 3½ hours. The solvent is evaporated, and the residue is treated with water. The water solution is then extracted with ether. The ether extract is washed with water, dried (MgSO$_4$), and evaporated to yield a yellow oil (21.21 g). Chromatography on silica gel (200 g) using an eluant of 3% ethyl acetate in light petroleum affords a colorless oil (19.69 g) of ethyl 2-bromodifluoromethyl-2-carbo-tert-butoxyphenylacetate:

NMR (CCl$_4$): δ 1.28, t (J=7 Hz), 3H; 1.52, s, 9H; 4.25, q (J=7Hz), 2H; 7.13–7.55, m, 5H.

The product is contaminated with ethyl 2-difluoromethyl-2-carbo-tert-butoxyphenylacetate and possibly with ethyl 2-dibromofluoromethyl-2-carbo-tert-butoxyphenylacetate.

(B) Ethyl 2-phenyl-3,3-difluoroacrylate

A solution of impure ethyl 2-bromodifluoro-2-carbo-tert-butoxyphenylacetate (20.95 g) in trifluoroacetic acid (44 ml) is stirred at room temperature for 1 hour. The solvent is removed by evaporation to give a pale-brown oil (17.29 g) which is then dissolved in THF (350 ml) and treated, with vigorous stirring, with 2 M aqueous sodium hydroxide (25.7 ml, 1 equivalent) for 15 minutes. The solution is then diluted with water and extracted with ether. The ether extract is washed with water, dried (MgSO$_4$) and evaporated. The residual yellow oil (10.80 g) is distilled to afford ethyl 2-phenyl-3,3-difluoroacrylate: colorless oil;

NMR (CCl$_4$): δ 1.25, t (J=7 Hz), 3H; 4.15, q (J=7 Hz), 2H; 7.18, s (broad), 5H.

The product may be contaminated with small amounts of ethyl 2-phenyl-3-fluoroacrylate and ethyl 2-phenyl-3-bromo-3-fluoroacrylate.

(C) 2-Phenyl-3,3-difluoroallyl alcohol

A solution of impure ethyl 2-phenyl-3,3-difluoroacrylate (7.13 g, 33.6 mmol) in THF (180 ml) is cooled to about −78° and treated with a solution of diisobutylaluminium hydride (136 mmol) in hexane (1 M solution). The cooling bath is removed and the temperature is allowed to rise to room temperature over about 45 minutes. The solution is again cooled (ca 5°) and methanol (50 ml) and then 10% aqueous potassium hydroxide (13.5 ml) are cautiously added. The mixture is then dried (MgSO$_4$) and filtered. Removal of solvent yields a yellow oil (4.60 g). Chromatography on silica gel (200 g) using 20% ethyl acetate in light petroleum gives two major products. The first-eluted compound is 2-phenyl-3,3-difluoroallyl alcohol (1.94 g), an almost colorless oil:

NMR (CCl$_4$): δ 2.70, s, 1H; 4.13 to 4.43, m, 2H; 6.98–7.35, m, 5H.

The oil is used without purification in the following step. The second-eluted compound is 2-phenyl-3-fluoroallyl alcohol (1.42 g). In addition to the above fraction, additional material (1.00 g), which is a mixture of the two compounds is obtained.

(D) 1,1-Difluoro-2-phenyl-3-phthalimidopropene

A solution of 2-phenyl-3,3-difluoroally alcohol (1.94 g), triphenylphosphine (2.99 g), and phthalimide (1.68 g) in THF (80 ml) is treated with a solution of diethyl azodicarboxylate (1.99 g) in THF (20 ml) at room temperature. The reaction is allowed to proceed about 16 hours. The THF is evaporated. Much of the by-product can be removed by its recrystallization from toluene and then from ether. The ether-soluble material (3.22 g) is purified by chromatography on silica gel (200 g) using 10% ethyl acetate in light petroleum. Recrystallization of the major portion (2.12 g) from hexane affords 1,1-difluoro-2-phenyl-3-phthalimidopropene: colorless needles; m.p. 102°–103°;

NMR (CCl$_4$): δ 4.67, m, 2H; 7.28, s (broad), 5H; 7.57 to 7.88, m, 4H.

Analysis for C$_{17}$H$_{11}$F$_2$NO$_2$: Found: C, 68.40; H, 3.78; N, 4.68% Requires: C, 68.22; H, 3.70; N, 4.68%

(E) 2-Phenyl-3,3-difluoroallylamine

A mixture of 1,1-difluoro-2-phenyl-3-phthalimidopropene (0.60 g) and hydrazine hydrate (0.11 g) in ethanol (4 ml) is vigourously stirred and refluxed for 1 hour. Water (4 ml) and concentrated hydrochloric acid (4 ml) are added, and the mixture is refluxed for another hour. The filtrate is washed with ether and evaporated to dryness to leave an almost colorless residue (0.41 g). The crude amine is purified via its N-tert-butoxycarbonyl derivative: colorless needles; m.p. 44°–45°;

NMR (CCl$_4$): δ 1.33, s, 9H; 3.93 to 4.27, m, 2H; 4.60, s (broad), 1H; 7.27, s, 5H.

Analysis for C$_{14}$H$_{17}$F$_2$NO$_2$: Found: C, 62.19; H, 6.28; N, 4.92% Requires: C, 62.44; H, 6.36; N, 5.20%

The N-tert-butoxycarbonyl derivative (0.14 g) is treated for about 16 hours at room temperature with a saturated solution of hydrogen chloride gas in dry ether (20 ml). After removal of solvent, the residue (0.18 g) is recrystallized from ethanol/diethyl ether to give 2-phenyl-3,3-difluoroallylamine, as the hydrochloride (0.07 g): colorless needles; m.p. 139°–140°;

NMR (D$_2$O): δ 4.10, s (broad), 2H; 7.43, s, 5H.

Analysis for C$_9$H$_{10}$ClF$_2$N: Found: C, 52.53; H, 5.00; N, 6.74% Requires: C, 52.57; H, 4.90; N, 6.81%

EXAMPLE 24

2-(3′-Hydroxy)phenylallylamine (A) 2-(3′-Methoxy)phenyl-3-bromopropene

A mixture of 2-(3′-methoxy)phenylpropene (3.00 g) and N-bromosuccinimide (3.60 g) in CCl$_4$ (1 ml) is heated at 180° (bath temperature) until a vigorous reaction occurs. The mixture is allowed to cool over 2 hours, after which it is mixed with more solvent. After filtration and evaporation of solvent, there is obtained a residual oil (4.18 g):

NMR (CDCl$_3$): δ 2.13, d (J=1.5 Hz); 3.70, s; 4.22, s; 5.42, d (J=3 Hz); 6.35, m, 6.57 to 7.37, m.

The oil is a mixture of 2-(3′-methoxy)phenyl-1-bromopropene (25%) and 2-(3′-methoxy)phenyl-3-bromopropene (75%). (B) 2-(3′-Methoxy)phenyl-3-phthalimidopropene A mixture of (0.43 g) containing 2-(3′-methoxy)phenyl-3-bromopropene (75%) and 2-(3′-methoxy)phenyl-1-bromopropene (25%) is treated with potassium phthalimide (2.77 g) in dimethyl formamide (35 ml) at 90° for 3 hours. Upon reaching room temperature, the reaction mixture is treated with ice-water, and the resulting mixture is extracted with CHCl$_3$. The organic layer is washed consecutatively with 10% aq. KOH, water, and brine. Upon drying and removal of solent by evaporation, there is obtained a colorless mass (3.62 g). Crystallization from n-hexane/CH$_2$Cl$_2$ affords 2-(3′-methoxy)phenyl-3-phthalimidopropene (3.11 g): colorless prisms; m.p. 118°–119°;

NMR (CDCl$_3$): δ 3.73, s, 3H; 4.60, s (broad), 2H; 5.10, s (broad), 1H; 5.40, s (broad), 1H; 6.60 to 7.30, m, 4H; 7.40 to 7.87, m, 4H.

Analysis for C$_{18}$H$_{15}$NO$_3$: Found: C, 73.81; H, 5.13; N, 4.65% Requires: C, 73.71; H, 5.15; N, 4.78%

(C) 2-(3′-Hydroxy)phenyl-3-phthalimidopropene

A solution of 2-(3′-methoxy)phenyl-3-phthalimidopropene (2.93 g) in CH$_2$Cl$_2$ (25 ml) at about −78° is treated with boron tribromide (2.76 g). The cooling bath is removed, and the mixture is stirred for 1 hour. It is then poured into ice-water and the mixture is stirred for another 30 minutes. The mixture is saturated with salt and extracted with CH$_2$Cl$_2$. The CH$_2$Cl$_2$ extract is washed with water, dried, and evaporated to give an orange oil (2.68 g). Chromatography on silica gel (120 g) using CH$_2$Cl$_2$ as eluant affords essentially pure 2-(3′-hydroxy)phenyl-3-phthalimidopropene (1.62 g): m.p. 108°–109°;

NMR (CDCl$_3$): δ 4.60, s (broad), 2H; 5.00, s (broad), 1H; 5.33, s (broad), 1H; 6.53 to 7.26, m, 4H; 7.50 to 7.93, m, 4H.

(D) 2-(3′-Hydroxy)phenylallylamine 2-(3′-Hydroxy)phenyl-3-phthalimidopropene (1.40 g) is treated with hydrazine hydrate (0.28 g) to give the crude amine, which is converted into the tert-butoxycarbonyl derivative. Essentially pure N-tert-butoxycarbonyl 2-(3′-hydroxy)phenylallylamine (0.63 g), m.p. 65°–66°, is obtained after chromathography on silica gel (30 g) using light petroleum (70%)/ether (30%) as eluant. Treatment of this compound with dry ether saturated with hydrogen chloride gives a precipitate of 3-(3′-hydroxy)phenylallylamine as the hydrochloride (0.50 g): colorless needles; m.p. 172°–173°;

Analysis for C$_9$H$_{12}$ClNO: Found: C, 58.04; H, 6.23; N, 7.48% Requires: C, 58.23; H, 6.52; N, 7.54%

EXAMPLE 25

(Z)-2-Phenyl-3-fluoroallylamine (A) 1,2-Dibromo-1-fluoro-2-phenyl-3-phthalimidopropane To a stirred solution of 1-fluoro-2-phenyl-3-phthalimidopropene (0.56 g) in $CH_2Cl_2$ (30 ml) in the absence of light and at 0° is added a solution of bromine (0.35 g) in $CH_2Cl_2$ (5 ml). The mixture is stirred for 24 hours after which the solution is decolorised by shaking with aqueous sodium sulfite. The organic layer is separated, dried, and evaporated to leave a colorless solid (0.88 g). Recrystallization from n-hexane/$CH_2Cl_2$ gives 1,2-dibromo-1-fluoro-2-phenyl-3-phthalimidopropane (0.66 g): colorless needles; m.p. 163°–164°;

NMR (CDCl$_3$): δ 4.50, m, 2H; 7.83, d (J=47 Hz), 1H; 7.07 to 7.90, m, 9H.

(B) (Z)-1-Fluoro-2-phenyl-3-phthalimidopropene

To a stirred solution of 1,2-dibromo-1-fluoro-2-phenyl-3-phthalimidopropane (0.66 g) in acetone (100 ml) is added solid sodium iodide (15 g). The mixture is refluxed for 4 hours, cooled, and decolorised by the addition of sufficient sodium sulfite. The acetone is evaporated to give a residue which is extracted with ether. The ether extract is then washed with water, dried, and evaporated to leave a colorless mass (0.34 g). Chromatography on silica gel (25 g) using light petroluem/ethyl acetate as eluant affords two pure substances. The first eluted is (Z)-1-fluoro-2-phenyl-3-phthalimidopropene (0.25 g), m.p. 78°–79°;

NMR (CDCl$_3$): δ 4.78, d.d. (J=3 Hz, 1.5 Hz), 2H; 6.80, d.t. (J=82 Hz, 1.5 Hz), 1H; 7.07 to 7.87, m, 9H.

Analysis for $C_{17}H_{12}FNO_2$: Found: C, 72.30; H, 4.63; N, 4.70% Requires: C, 72.59; H, 4.30; N, 4.98%

The second product is (E)-1-fluoro-2-phenyl-3-phthalimidopropene (0.08 g).

(C) (Z)-2-Phenyl-3-fluoroallylamine (Z)-1-Fluoro-2-phenyl-3-phthalimidopropene (0.25 g) is treated with hydrazine hydrate (50 mg) in ethanol (2 ml), and then concentrated hydrochloric acid (2 ml) and water (2 ml). Recrystallization of the resulting product (0.19 g) from ethanol/ether affords pure (Z)-2-phenyl-3-fluoroallylamine, as the hydrochloride: m.p. 145°;

NMR (D$_2$O): δ 4.20, d (broad, J=3 Hz), 2H; 7.13, d (J=82 Hz), 1H; 7.50, m, 5H.

Analysis for $C_9H_{11}ClFN$: Found: C, 57.60; H, 5.91; N, 7.52% Requires: C, 57.61; H, 5.91; N, 7.46%

EXMPLE 26

(E)-2-(4'-Methoxy)phenyl-3-chloroallylamine (A) Ethyl 2-chloromethyl-2-carbo-tert-butoxy(4'-methoxy)phenylacetate A solution of ethyl 2-carbo-tert-butoxy(4'-methoxy)phenylacetate (11.80 g) in THF (120 ml) is cooled to about −70° and treated consecutatively with potassium tert-butoxide (4.93 g) and n-butyllithium (33 ml, 50 mmol). The solution is stirred for 30 minutes, after which the cooling bath is removed and the temperature is allowed to rise over 1 hour. The solution is then heated to 45°. Chloroform (12 g) is added dropwise over 15 minutes and the mixture is refluxed for 2 hours, cooled, poured into water, and extracted with ether. The ether extract is washed with water, dried, and evaporated to leave a dark oil (15.65 g). A small portion is purified by silica gel chromatography to give ethyl 2-chloromethyl-2-carbo-tert-butoxy(4'-methoxy)phenylacetate: colorless oil; b.p. 119°–120°/0.05 mm;

NMR (CDCl$_3$): δ 1.30, t (J=7 Hz), 3H; 1.48, s, 9H; 3.80, s, 3H; 4.28, q (J=7 Hz), 2H; 6.60, s, 1H; centred at 7.17, A$_2$B$_2$ (J$_{AB}$=9 Hz), 4H.

Analysis for $C_{17}H_{22}Cl_2O_5$: Found: C, 54.16; H, 5.79% Requires: C, 54.12; H, 5.87%

(B) Ethyl (E)-2-(4'-methoxy)phenyl-3-chloroacrylate

Ethyl 2-chloromethyl-2-carbo-tert-butoxy(4'-methoxy)phenylacetate is treated according to the procedure of Example 8 to give ethyl (E)-2-(4'-methoxy)phenyl-3-chloroacrylate; b.p. 94°–95°/0.05 mm;

NMR (CDCl$_3$): δ 1.20, t (J=7 Hz), 3H; 3.67, s, 3H; 4.13, q (J=7 Hz), 2H; centred at 7.00, A$_2$B$_2$ (J=9 Hz), 4H; 7.43, s, 1H.

Analysis for $C_{12}H_{13}ClO_3$: Found: C, 59.88; H, 5.32% Requires: C, 59.88; H, 5.44%

(C) (E)-2-(4'-Methoxy)phenyl-3-chloroallyl alcohol

A solution of ethyl (E)-2-(4'-methoxy)phenyl-3-chloroacrylate (4.80 g) in hexane (50 ml) is added dropwise to a solution of diisobutylaluminium hydride (60 mmol) in hexane so that the temperature remains below 20°. The mixture is stirred for 2 hours, cooled, in an ice-bath, and treated consecutatively with methanol (8 ml) and 10% aqueous sulfuric acid (to give a pH of 4–5). The layers are separated, and the hexane layer is washed with water, dried, and evaporated. The residue is crystallized from light petroleum/ether to obtain 2-(4'-methoxy)phenyl-3-chloroallyl alcohol (3.10 g): colorless needles; m.p. 58°–59°;

NMR (CDCl$_3$): δ 3.10, s (broad), 1H; 3.73, s, 1H; 4.23, s (broad), 2H; 6.27, s (broad), 1H; centred at 7.07, A$_2$B$_2$ (J=9 Hz), 4H.

(D) (E)-1-Chloro-2-(4'-methoxy)phenyl-3-phthalimidopropene (E)-2-(4'-Methoxy)phenyl-3-chloroallyl alcohol is treated according to the procedure of Example 12 to give (E)-1-chloro-2-(4'-methoxy)phenyl-3-phthalimidopropene; m.p. 154°–155°.

NMR (CDCl$_3$): δ 3.70, s, 3M; 4.53, m, 2H, 6.32, m, 1H; centred at 7.07, A$_2$B$_2$ (J=9 Hz), 4H; 7.43 to 7.83, m, 4H.

Analysis for $C_{18}H_{14}ClNO_2$: Found: C, 65.91; H, 4.51; N, 4.20% Requires: C, 65.96; H, 4.30; N, 4.27%

(E)-2-(4'-Methoxy)phenyl-3-chloroallylamine (E)-1-Chloro-2-(4'-methoxy)phenyl-3-phthalimidopropene is treated according to the procedure of Example 14 to give 2-(4'-methoxy)phenyl-3-chloroallylamine as the hydrochloride: m.p. 150°–152°;

NMR (D$_2$O+DCL): δ 3.87, s, 3H; 4.08, s, 2H; 6.78, s, 1H; centred at 7.27, A$_2$B$_2$ (J=9 Hz), 4H;

Analysis for $C_{10}H_{13}Cl_2NO$: Found: C, 51.05; H, 5.39; N, 5.86% Requires: C, 51.30; H, 5.59; N, 5.98%

EXAMPLE 27

2-(3'-Methoxy)phenylallylamine hydrochloride 2-(3'-Methoxy)phenyl-3-phthalimidopropene is treated with hydrazine hydrate to give the crude amine which is purified by its N-protected derivative, N-tert-butoxycarbonyl 2-(3'-methoxy)phenylallylamine:

NMR (CDCl$_3$): δ 1.43, s, 9H; 4.07, d (J=6 Hz), 2H; 4.83, t (J=6 Hz), 1H; 5.13, s, 1H; 5.32, s, 1H; 6.63 to 7.30, m, 4H; 7.50, s, 1H.

Treatment of this derivative with ether/hydrogen chloride gives 2-(3'-methoxy)phenylallylamine, as the hydrochloride: colorless needles, m.p. 136°;

NMR (D$_2$O): δ 3.87, s, 3H; 4.13, s (broad), 2H; 5.50, t (J=1.5 Hz), 1H; 5.70, s, 1H; 6.87 to 7.60, m, 4H.

Analysis for $C_{10}H_{14}ClNO$: Found: C, 60.05; H, 6.84; N, 6.93% Requires: C, 60.15; H, 7.07; N, 7.01%

The following Examples (28–31) illustrate and describe the testing of the compounds of this invention for their ability to inhibit MAO enzyme.

EXAMPLE 28

Inhibition of MAO—In vitro testing (A) The ability of a compound of Formula I or II to inhibit MAO can be determined in vitro by the method of A. Christmas et al, Br. J. Pharmacol. 45, 490 (1972) in partially purified mitochondria from rat brain using $^{14}C$ p-tyramine as the substrate. The MAO inhibitory activity of a compound is expressed as the "$IC_{50}$" value, which is the molar concentration required to produce 50% inhibition of the enzyme. The $IC_{50}$ values for certain compounds of Formula I or II were determined using the above-described method, and the results are set forth in Table I. For comparison, $IC_{50}$ values for clorgyline, L-deprenyl, and pargyline are also given. The data shown in Table I does not show selectivity of the compounds against MAO-A or MAO-B inhibitors, since $^{14}C$ p-tyramine is a substrate for both forms of the enzyme.

TABLE I

| MAO inhibitory activity - In vitro | |
|---|---|
| Compound[a] | $IC_{50}$ (moles) |
| (E)-2-phenyl-3-fluoroallylamine | $7 \times 10^{-7}$ |
| (E)-2-(3',4'-dimethoxy)phenyl-3-fluoroallylamine | $2.5 \times 10^{-6}$ |
| (E)-2-(4'-methoxy)phenyl-3-fluoroallylamine | $6 \times 10^{-8}$ |
| (E)-2-(3'-methoxy)phenyl-3-fluoroallylamine | $5 \times 10^{-9}$ |
| (E)-2-(2'-methoxy)phenyl-3-fluoroallylamine | $2.5 \times 10^{-6}$ |
| (E)-2-(4'-methoxy)benzyl-3-fluoroallylamine | $3 \times 10^{-6}$ |
| (E)-2-benzyl-3-fluoroallylamine | $7.5 \times 10^{-6}$ |
| (E)-2-(4'-chloro)phenyl-3-fluoroallylamine | $2 \times 10^{-8}$ |
| (E)-2-(3'-hydroxy)phenyl-3-fluoroallylamine | $5 \times 10^{-8}$ |
| (E)-2-(3'-trifluoromethyl)phenyl-3-fluoroallylamine | $7 \times 10^{-9}$ |
| (E)-N—ethyl 2-(3',4'-dimethoxy)phenyl-3-fluoroallylamine | $7 \times 10^{-5}$ |
| (E)-N—ethyl 2-(3'-methoxy)phenyl-3-fluoroallylamine | $3 \times 10^{-6}$ |
| (Z)-2-phenyl-3-fluoroallylamine | $1 \times 10^{-6}$ |
| 2-phenyl-3,3-difluoroallylamine | $1 \times 10^{-5}$ |
| 2-phenylallylamine | $4 \times 10^{-4}$ |
| 2-(3-methoxy)phenylallylamine | $1 \times 10^{-5}$ |
| 2-(3-hydroxy)phenylallylamine | $2.5 \times 10^{-7}$ |
| 2-phenyl-3-bromoallylamine | $4 \times 10^{-5}$ |
| (E)-2-phenyl-3-chloroallylamine | $1 \times 10^{-4}$ |
| (Z)-2-phenyl-3-chloroallylamine | $5 \times 10^{-4}$ |
| 2-phenyl-3,3-dibromoallylamine | $5 \times 10^{-4}$ |
| clorgyline | $1 \times 10^{-7}$ |
| L-deprenyl | $1 \times 10^{-7}$ |
| pargyline | $2 \times 10^{-6}$ |

[a]Tested as hydrochloride salt.

The data shown in Table I demonstrate that the compounds tested are potent inhibitors of MAO.

(B) The compounds of Formula I or II can be tested to determine whether or not the MAO inhibition follows time-dependent kinetics by the procedure described below:

Mitochondria are prepared from rat brain by homogenation in phosphate buffer (0.1 M, pH 7.2) followed by differential centrifugation. The mitochondria are suspended in the same buffer, the test compound is added at the desired concentration, and the system is incubated. At different time intervals, aliquots are taken and MAO activity is measured using $^{14}C$ p-tyramine (a mixed substrate) as the substrate (See A. Christmas, et al, supra). When the compounds shown in Table I were tested according to the above-described procedure, the MAO inhibitory activity increased as a function of time of incubation. The initial rate of decrease of activity increased with increasing concentration of inhibitor. (Z)-2-Phenyl-3-chloroallylamine did not show time-dependent inhibitory kinetics. The inhibition of MAO was shown to be irreversible since dialysis against phosphate buffer (24 hours) did not restore enzyme activity.

(C) The selectivity of a compound of Formula I or II with respect to inhibition of MAO-A and MAO-B can be determined by repeating the procedure of Part B and measuring the MAO activity using both $^{14}C$ 5-hydroxytryptamine (a preferred substrate for MAO-A) and $^{14}C$ phenethylamine (a preferred substrate for MAO-B) as the substrate in place of $^{14}C$ p-tyramine (a mixed substrate). Certain compounds of Formula I or II were tested for MAO selectivity according to the above-described procedure and the results shown in Table II were obtained. Selectivity is expressed as the ratio of the inhibitory activity against MAO-B versus the inhibitory activity against MAO-A.

TABLE II

| Selectivity of MAO inhibitors - In vitro | |
|---|---|
| Compound | Selectivity $\left(\dfrac{\text{MAO-B}}{\text{MAO-A}}\right)$ |
| (E)-2-(4'-methoxy)phenyl-3-fluoroallylamine | 1000 |
| (E)-2-(3', 4'-dimethoxy)phenyl-3-fluoroallylamine | 1000 |
| (E)-2-(4'-methoxy)benzyl-3-fluoroallylamine | 500 |
| (E)-2-phenyl-3-fluoroallylamine | 10 |
| (E)-2-benzyl-3-fluoroallylamine | 200 |
| (E)-2-(3'-methoxy)phenyl-3-fluoroallylamine | 4 |
| (E)-2-(4'-chloro)phenyl-3-fluoroallylamine | 10 |
| clorgyline | 0.001 |
| L-deprenyl | 100 |
| pargyline[a] | 10 |

[a]literature figure.

The results in Table II indicate that (E)-2-(4'-methoxy)phenyl-3-fluoroallylamine, (E)-2-(3',4'-dimethoxy)phenyl-3-fluoroallylamine, (E)-2-(4'-methoxy)benzyl-3-fluoroallylamine, and (E)-2-benzyl-3-fluoroallylamine have marked selectivity for MAO-B as compared to MAO-A.

EXAMPLE 29

Inhibition of MAO—Ex vivo

The ability of a compound of Formula I or II to inhibit MAO can be determined ex vivo by the following procedure:

The test compound is administered intraperitoneally (ip), intravenously (iv), or orally (po) to rats or mice and the animals are killed at various times after treatment. The brain, heart, liver, or duodenum is removed and either a crude homogenate or a mitochondrial fraction, described in Example 28, Part A, is prepared. MAO activity is determined in the homogenates using $^{14}C$ p-tyramine, as the substrate. Table III gives the results of the testing of certain compounds according to the above-described procedure. Selectivity can be determined by repeating the above-described test using either $^{14}C$ 5-hydroxytryptamine (for MAO-A) or $^{14}C$ phenethylamine (for MAO-B) as the substrate for determining the % inhibition

TABLE III

% Inhibition of MAO - Ex vivo

| Compound | Dose (mg/kg) | Animal | Time (hr) | % Inhibition[1] | | | |
|---|---|---|---|---|---|---|---|
| | | | | Brain | Heart | Liver | Duodenum |
| (E)-2-phenyl-3-fluoro-allylamine | 0.1 (iv) | rat | 24 | — | 85 | 48 | 67 |
| | 0.5 (ip) | mouse | 24 | 45 | 91 | — | — |
| | 1.0 (ip) | mouse | 24 | 68 | 97 | — | — |
| (E)-2-(3',4'-dimethoxy)-phenyl-3-fluoroallyl-amine | 0.5 (po) | rat | 18 | 79 | — | — | — |
| | 1.0 (iv) | rat | 2 | — | 17 | 58 | 40 |
| | 2.5 (po) | rat | 18 | 88 | — | — | — |
| | 10.0 (po) | rat | 18 | 93 | — | — | — |
| (E)-2-(4'-methoxy)-phenyl-3-fluoroallyl-amine | 0.1 (iv) | rat | 2 | — | 50 | 30 | 80 |
| | 0.25 (po) | rat | 18 | 75 | — | — | — |
| | 1.0 (po) | rat | 18 | 86 | — | — | — |
| | 5.0 (po) | rat | 18 | 97 | — | — | — |
| (E)-2-(3'-methoxy)phenyl-3-fluoroallyl-amine | 0.1 (iv) | rat | 2 | — | 98 | 70 | 90 |
| clorgyline | 0.1 (iv) | rat | 2 | — | 84 | — | 87 |
| | 0.25 (po) | rat | 18 | 1 | — | — | — |
| | 1.0 (po) | rat | 18 | 20 | — | — | — |
| | 5.0 (po) | rat | 18 | 64 | — | — | — |
| L-deprenyl | 0.5 (po) | rat | 18 | 16 | — | — | — |
| | 1.0 (po) | rat | 2 | — | 48 | 91 | 62 |
| | 5.0 (po) | rat | 18 | 39 | — | — | — |
| | 10.0 (po) | rat | 18 | 88 | — | — | — |

[1] determined by using $^{14}C$ p-tryamine as substrate.

EXAMPLE 30

Inhibition of MAO-In vivo

The ability of a compound of Formula I or II to inhibit MAO can be determined in vivo in mice according to the following procedure, wherein changes in concentration of the following procedure, wherein changes in concentration of the endogenous MAO substrates and the metabolites thereof are assayed.

Mice are given an intraperitoneal injection of the test compound and 2 hours or 16 hours later the animals are killed. The levels of dopamine, dihydroxyphenylacetic acid (DOPAC), 5-hydroxytryptamine (5-HT), and 5-hydroxyindole-3-acetic acid (5-HIAA) in brain homogenates are determined by the method of J. Wagner et al, J. Chromatog. 164, 41 (1979) and P. Bey et al, Br. J. Pharmac., 70, 571 (1980). When certain compounds of Formula I or II are tested according to the above-described procedure, the results given in Table IV are obtained:

TABLE IV

| Compound | Dose (mg/kg) | Time (hr) | % Change (compared to control) | | | |
|---|---|---|---|---|---|---|
| | | | Dopamine | DOPAC | 5-HT | 5-HIAA |
| (E)-2-phenyl-3-fluoroallyl-amine | 1 (ip) | 2 | +15 | −67 | +41 | −35 |
| | 10 (ip) | 2 | +32 | −92 | +90 | −90 |
| | 100 (ip) | 2 | +19 | −95 | +96 | −91 |
| (E)-2-(3', 4'-dimethoxy)phenyl-3-fluoroallylamine | 10 (ip) | 16 | +18 | −62 | +31 | −8 |
| | 50 (ip) | 16 | +22 | −85 | +122 | −32 |
| | 100 (ip) | 16 | +25 | −85 | +150 | −36 |
| L-deprenyl | 10 (ip) | 2 | +10 | −21 | +18 | +9 |

EXAMPLE 31

The following test procedure can be employed to assess the potential of a compound of Formula I or II for producing the "cheese effect":

Rats are administered an intravenous injection of the test compound at various dosage levels, and 30 minutes later the rats are challenged with several intravenous or intraduodenal dodes of p-tyramine. The heart rate response is measured. Compounds having the "cheese effect" will potentiate the heart rate response to p-tyramine. The results of the testing of certain compounds of Formula I or II are shown below in Table V, where the values given represent the factors by which the heart-rate response to p-tyramine is increased after administration of the test compound.

TABLE V

Potentiation of heart-rate response to p-tyramine

| Compound | Dose (iv) | Route of administration of p-tyramine | Potentiation of heart-rate response to p-tyramine |
|---|---|---|---|
| (E)-2-(4'-methoxy)phenyl-3-fluoro-allylamine | 0.1 | i.v. | 1.4 fold |
| | 1.0 | i.v. | 5.2 fold |
| | 0.1 | i.d. | 2.0 fold |
| | 1.0 | i.d. | 4.6 fold |
| (E)-2-(3', 4'-dimethoxy)phenyl-3-fluoroallylamine | 1.0 | i.v. | 2.3 fold |
| | 1.0 | i.d. | 2.5 fold |
| (E)-2-phenyl-3-fluoroallylamine | 0.1 | i.v. | 8.4 fold |
| | 0.1 | i.d. | 9.1 fold |
| L-deprenyl | 0.1 | i.v. | 1.3 fold |
| | 1.0 | i.v. | 2.2 fold |
| | 0.1 | i.d. | no effect |
| | 1.0 | i.d. | 2.1 fold |
| clorgyline | 0.1 | i.v. | 5.2 fold |

TABLE V-continued

| Potentiation of heart-rate response to p-tyramine | | | |
|---|---|---|---|
| Compound | Dose (iv) | Route of administration of p-tyramine | Potentiation of heart-rate response to p-tyramine |
| | 0.1 | i.d. | 5.6 fold | i.v.: tyramine administered intravenously
i.d.: tyramine administered intraduodenally

What is claimed is:

1. A compound of the formula:

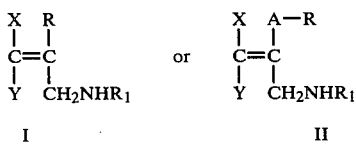

wherein:
(a) X is fluorine and Y is hydrogen,
(b) Y is fluorine and X is hydrogen, or
(c) X is fluorine and Y is fluorine;
R is phenyl; phenyl monosubstituted, disubstituted, or trisubstituted by $C_1$–$C_8$alkyl, $C_1$–$C_8$alkoxy, hydroxy, chlorine, bromine, iodine, fluorine, trifluoromethyl, nitro, $C_1$–$C_6$alkylcarbonyl, benzoyl, or phenyl; 1- or 2-naphthyl; 1-, 2-, or 3-indenyl; 1-, 2-, or 9-fluorenyl; 1-, 2-, or 3-piperidinyl; 2- or 3-pyrrolyl; 2- or 3-thienyl; 2- or 3-furanyl; 2- or 3-indolyl; 2- or 3-thianaphthenyl; or 2- or 3-benzofuranyl;
$R_1$ is hydrogen, $C_1$–$C_8$alkyl, benzyl, or phenethyl; and
A is a divalent radical of the formula:

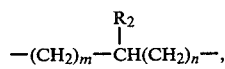

wherein $R_2$ is hydrogen, methyl, or ethyl, and m and n, independently, are an integer from 0 to 4, provided that m+n cannot be greater than 4; —$(CH_2)_p$—D—$(CH_2)_q$—, wherein D is oxygen or sulfur, p is an integer from 2 to 4, and q is an integer from 0 to 2, provided that p+q cannot be greater than 4; or —$(CH_2)_r$CH=CH$(CH_2)_s$—, wherein r is an integer from 1 to 3 and s is an integer from 0 to 2, provided that r+s cannot be greater than 3; or a non-toxic, pharmaceutically acceptable acid addition salt thereof.

2. A compound of Formula I as defined in claim 1.

3. A compound as defined in claim 2 wherein R is phenyl.

4. A compound as defined in claim 2 wherein R is phenyl monosubstituted, disubstituted, or trisubstituted by ($C_1$–$C_8$)alkyl, ($C_1$–$C_8$)alkoxy, hydroxy, chlorine, bromine, iodine, fluorine, trifluoromethyl, nitro, ($C_1$–$C_8$)alkylcarbonyl, benzoyl, or phenyl.

5. A compound as defined in claim 4 wherein R is phenyl monosubstituted by ($C_1$–$C_8$)alkoxy.

6. A compound as defined in claim 5 wherein R is phenyl monosubstituted by methoxy.

7. A compound as defined in claim 4 wherein R is phenyl disubstituted by ($C_1$–$C_8$)alkoxy.

8. A compound as defined in claim 7 wherein R is phenyl disubstituted by methoxy.

9. A compound as defined in claim 4 wherein R is phenyl monosubstituted by hydroxy.

10. A compound as defined in claim 4 wherein R is phenyl disubstituted by hydroxy.

11. A compound as defined in claim 4 wherein R is phenyl monosubstituted by fluorine, chlorine, bromine, iodine, or trifluoromethyl.

12. A compound as defined in claim 4 wherein R is phenyl disubstituted by fluorine, chlorine, bromine, or iodine.

13. A compound as defined in claim 2 wherein R is 1- or 2-naphthyl; 1-, 2-, or 3-indenyl; 1-, 2-, or 9-fluorenyl; 1-, 2-, or 3-piperidinyl; 2- or 3-pyrrolyl; 2- or 3-thienyl; 2- or 3-furanyl; 2- or 3-indolyl; 2- or 3-thianaphthenyl; or 2- or 3-benzofuranyl.

14. A compound as defined in claim 13 wherein R is 1- or 2-naphthyl.

15. A compound as defined in claim 13 wherein R is 2- or 3-furanyl.

16. A compound as defined in claim 2, 3, 4, 5, 6, 7, 8, 9, 10, 11, 12, 13, 14, or 15 wherein:
(a) X is hydrogen and Y is fluorine; or
(b) X is fluorine and Y is hydrogen.

17. A compound as defined in claim 16 wherein $R_1$ is hydrogen.

18. The compound as defined in claim 17 which is (Z)- or (E)-2-phenyl-3-fluoroallylamine.

19. The compound as defined in claim 17 which is 2-phenyl-3,3-difluoroallyamine.

20. The compound as defined in claim 17 which is (Z)- or (E)-2-(2'-methoxy)phenyl-3-fluoroallylamine.

21. The compound as defined in claim 17 which is (Z)- or (E)-2-(3'-methoxy)phenyl-3-fluoroallylamine.

22. The compound as defined in claim 17 which is (Z)- or (E)-2-(4'-methoxy)phenyl-3-fluoroallylamine.

23. The compound as defined in claim 17 which is (Z)- or (E)-2-(3'-hydroxy)phenyl-3-fluoroallylamine.

24. The compound as defined in claim 17 which is (Z)- or (E)-N-ethyl 2-(3'-methoxy)phenyl-3-fluoroallylamine.

25. The compound as defined in claim 17 which is (Z)- or (E)-2-(3',4'-dimethoxy)phenyl-3-fluoroallylamine.

26. The compound as defined in claim 17 which is (Z)- or (E)-N-ethyl 2-(3',4'-dimethoxy)phenyl-3-fluoroallylamine.

27. The compound as defined in claim 17 which is (Z)- or (E)-2-(4'-chloro)phenyl-3-fluoroallylamine.

28. The compound as defined in claim 17 which is (Z)- or (E)-2-(3'-trifluoromethyl)phenyl-3-fluoroallylamine.

29. A compound as defined in claim 17 which is (Z)- or (E)-2-(α-naphthyl)-3-fluoroallylamine or (Z)- or (E)-2-(β-naphthyl)-3-fluoroallylamine.

30. A compound of Formula II as defined in claim 1.

31. A compound as defined in claim 30 wherein R is phenyl.

32. A compound as defined in claim 30 wherein R is phenyl monosubstituted, disubstituted, or trisubstituted by ($C_1$–$C_8$)alkyl, ($C_1$–$C_8$)alkoxy, hydroxy, chlorine, bromine, iodine, fluorine, trifluoromethyl, nitro, ($C_1$–$C_8$)alkylcarbonyl, benzoyl, or phenyl.

33. A compound as defined in claim 32 wherein R is phenyl monosubstituted by ($C_1$–$C_8$)alkoxy.

34. A compound as defined in claim 33 wherein R is phenyl monosubstituted by methoxy.

35. A compound as defined in claim 32 wherein R is phenyl disubstituted by ($C_1$–$C_8$)alkoxy.

36. A compound as defined in claim 35 wherein R is phenyl disubstituted by methoxy.

37. A compound as defined in claim 32 wherein R is phenyl monosubstituted by hydroxy.

38. A compound as defined in claim 32 wherein R is phenyl disubstituted by hydroxy.

39. A compound as defined in claim 32 wherein R is phenyl monosubstituted by fluorine, chlorine, bromine, iodine, or trifluoromethyl.

40. A compound as defined in claim 32 wherein R is phenyl disubstituted by fluorine, chlorine, bromine, or iodine.

41. A compound as defined in claim 30 wherein R is 1- or 2-naphthyl; 1-, 2-, or 3-indenyl; 1-, 2-, or 9-fluorenyl; 1-, 2-, or 3-piperidinyl; 2- or 3-pirrolyl; 2- or 3-thienyl; 2- or 3-furanyl; 2- or 3-indolyl; 2- or 3-thianaphthenyl; or 2- or 3-benzofuranyl.

42. A compound as defined in claim 41 wherein R is 1- or 2-naphthyl.

43. A compound as defined in claim 41 wherein R is 2- or 3-furanyl.

44. A compound as defined in claim 30, 31, 32, 33, 34, 35, 36, 37, 38, 39, 40, 41, 42, or 43 wherein A is —CH$_2$—.

45. A compound as defined in claim 30, 31, 32, 33, 34, 35, 36, 37, 38, 39, 40, 41, 42, or 43 wherein:
 (a) X is hydrogen and Y is fluorine; or
 (b) X is fluorine and Y is hydrogen.

46. A compound as defined in claim 45 wherein R$_1$ is hydrogen.

47. A compound as defined in claim 45 wherein A is —CH$_2$—.

48. A compound as defined in claim 45 wherein R$_1$ is hydrogen and A is —CH$_2$—.

49. The compound as defined in claim 48 which is (Z)- or (E)-2-benzyl-3-fluoroallylamine.

50. The compound as defined in claim 48 which is (Z)- or (E)-2-(4'-methoxy)benzyl-3-fluoroallylamine.

51. The compound as defined in claim 48 which is (Z)- or (E)-2-(3',4'-dimethoxy)benzyl-3-fluoroallylamine.

52. A compound of the formula:

$$\begin{array}{cc} X & Ra \\ | & | \\ C=C \\ | & | \\ Y & CH_2Q \end{array}$$

wherein:
 (a) X is fluorine and Y is hydrogen,
 (b) Y is fluorine and X is hydrogen, or
 (c) X is fluorine and Y is fluorine;
Ra is R or —AR, wherein:
R is phenyl; phenyl monosubstituted, disubstituted, or trisubstituted by C$_1$–C$_8$alkyl, C$_1$–C$_8$alkoxy, hydroxy, chlorine, bromine, iodine, fluorine, trifluoromethyl, nitro, C$_1$–C$_6$alkylcarbonyl, benzoyl, or phenyl; 1- or 2-naphthyl; 1-, 2-, or 3-indenyl; 1-, 2-, or 9-fluorenyl; 1-, 2-, or 3-piperidinyl; 2- or 3-pyrrolyl; 2- or 3-thienyl; 2- or 3-furanyl; 2- or 3-indolyl; 2- or 3-thianaphtenyl; or 2- or 3-benzofuranyl;
A is a divalent radical of the formula:

$$-(CH_2)_m-\underset{\underset{R_2}{|}}{CH}(CH_2)_n-,$$

wherein R$_2$ is hydrogen, methyl, or ethyl, and m and n, independently, are an integer from 0 to 4, provided that m+n cannot be greater than 4; —(CH$_2$)$_p$—D—(CH$_2$)$_q$—, wherein D is oxygen or sulfur, p is an integer from 2 to 4, and q is an integer from 0 to 2, provided that p+q cannot be greater than 4; or —(CH$_2$)$_r$CH=CH(CH$_2$)$_s$—, wherein r is an integer from 1 to 3 and s is an integer from 0 to 2, provided that r+s cannot be greater than 3; and Q is hydroxy or a leaving group.

53. The compound as defined in claim 52 which is (E)-2-(2'-methoxy)phenyl-3-fluoroallyl alcohol.

54. The compound as defined in claim 52 which is (E)-2-(3'-methoxy)phenyl-3-fluoroallyl alcohol.

55. The compound as defined in claim 52 which is (E)-2-(4'-methoxy)phenyl-3-fluoroallyl alcohol.

56. The compound as defined in claim 52 which is (E)-2-(3',4'-dimethoxy)phenyl-3-fluoroallyl alcohol.

57. The compound as defined in claim 52 which is (E)-2-(2'-methoxy)benzyl-3-fluoroallyl alcohol.

58. The compound as defined in claim 52 which is (E)-2-(3'-methoxy)benzyl-3-fluoroallyl alcohol.

59. The compound as defined in claim 52 which is (E)-2-(4'-methoxy)benzyl-3-fluoroallyl alcohol.

60. The compound as defined in claim 52 which is (E)-2-phenyl-3-fluoroallyl alcohol.

61. The compound as defined in claim 52 which is (E)-2-benzyl-3-fluoroallyl alcohol.

62. The compound as defined in claim 52 which is (E)-2-(3',4'-dimethoxy)benzyl-3-fluoroallyl alcohol.

63. A method for treating depression which comprises administering to a depressed patient an effective amount of a compound of the formula:

$$\begin{array}{cc} X & R \\ | & | \\ C=C \\ | & | \\ Y & CH_2NHR_1 \end{array} \quad \text{or} \quad \begin{array}{cc} X & A-R \\ | & | \\ C=C \\ | & | \\ Y & CH_2NHR_1 \end{array}$$

I  II wherein:
 (a) X is fluorine and Y is hydrogen,
 (b) Y is fluorine and X is hydrogen, or
 (c) X is fluorine and Y is fluorine;
R is phenyl; phenyl monosubstituted, disubstituted, or trisubstituted by C$_1$–C$_8$alkyl, C$_1$–C$_8$alkoxy, hydroxy, chlorine, bromine, iodine, fluorine, trifluoromethyl, nitro, C$_1$–C$_6$alkylcarbonyl, benzoyl, or phenyl; 1- or 2-naphthyl; 1-, 2-, or 3-indenyl; 1-, 2-, or 9-fluorenyl; 1-, 2-, or 3-piperidinyl; 2- or 3-pyrrolyl; 2- or 3-thienyl; 2- or 3-furanyl; 2- or 3-indolyl; 2- or 3-thianaphtenyl; or 2- or 3-benzofuranyl;
R$_1$ is hydrogen, C$_1$–C$_8$alkyl, benzyl, or phenethyl; and
A is a divalent radical of the formula:

$$-(CH_2)_m-\underset{\underset{R_2}{|}}{CH}(CH_2)_n-,$$

wherein R$_2$ is hydrogen, methyl, or ethyl, and m and n, independently, are an integer from 0 to 4, provided that m+n cannot be greater than 4; —(CH$_2$)$_p$—D—(CH$_2$)$_q$—, wherein D is oxygen or sulfur, p is an integer from 2 to 4, and q is an integer from 0 to 2, provided that p+q cannot be greater than 4; or —(CH$_2$)$_r$CH=CH(CH$_2$)$_s$—, wherein r is an integer from 1 to 3 and s is an integer from 0 to 2, provided that r+s cannot be greater than 3; or a non-toxic, pharmaceutically acceptable acid addition salt thereof.

64. The method as defined in claim 63 wherein the compound is (Z)- or (E)-2-(4'-methoxy)phenyl-3-fluoroallylamine.

65. The method as defined in claim 63 wherein the compound is (Z)- or (E)-2-(3',4'-dimethoxy)phenyl-3-fluoroallylamine.

66. A pharmaceutical composition comprising:
(a) a compound of the formula:

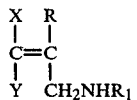  or  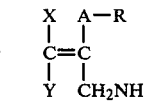

I   II wherein:
(a) X is fluorine and Y is hydrogen,
(b) Y is fluorine and X is hydrogen, or
(c) X is fluorine and Y is fluorine;
R is phenyl; phenyl monosubstituted, disubstituted, or trisubstituted by $C_1$–$C_8$alkyl, $C_1$–$C_8$alkoxy, hydroxy, chlorine, bromine, iodine, fluorine, trifluoromethyl, nitro, $C_1$–$C_6$alkylcarbonyl, benzoyl, or phenyl; 1- or 2-naphthyl; 1-, 2-, or 3-indenyl; 1-, 2-, or 9-fluorenyl; 1-, 2-, or 3-piperidinyl; 2- or 3-pyrrolyl; 2- or 3-thienyl; 2- or 3-furanyl; 2- or 3-indolyl; 2- or 3-thianaphtenyl; or 2- or 3-benzofuranyl;
$R_1$ is hydrogen, $C_1$–$C_8$alkyl, benzyl, or phenethyl; and A is a divalent radical of the formula:

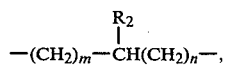

wherein $R_2$ is hydrogen, methyl, or ethyl, and m and n, independently, are an integer from 0 to 4, provided that m+n cannot be greater than 4; —$(CH_2)_p$—D—$(CH_2)_q$—, wherein D is oxygen or sulfur, p is an integer from 2 to 4, and q is an integer from 0 to 2, provided that p+q cannot be greater than 4; or —$(CH_2)_r$CH=CH$(CH_2)_s$—, wherein r is an integer from 1 to 3 and s is an integer from 0 to 2, provided that r+s cannot be greater than 3; or a non-toxic, pharmaceutically acceptable acid addition salt thereof (b) a pharmaceutically acceptable carrier.

67. A pharmaceutical composition as defined in claim 66 wherein the compound is (Z)- or (E)-2-(3'-methoxyphenyl)-3-fluoroallylamine.

68. A pharmaceutical composition as defined in claim 66 wherein the compound is (Z)- or (E)-2-(3',4'-dimethoxyphenyl)-3-fluoroallylamine.

* * * * *

REEXAMINATION CERTIFICATE (1884th)

United States Patent [19]

Bey

[11] B1 4,454,158

[45] Certificate Issued Dec. 22, 1992

[54] ALLYL AMINE MAO INHIBITORS

[75] Inventor: Philippe Bey, Strasbourg, France

[73] Assignee: Merrell Toraude et Compagnie, Strasbourg, France

Reexamination Request:
No. 90/002,411, Aug. 20, 1991

Reexamination Certificate for:
Patent No.: 4,454,158
Issued: Jun. 12, 1984
Appl. No.: 268,555
Filed: Jun. 1, 1981

[51] Int. Cl.$^5$ ............................................. A01N 33/02
[52] U.S. Cl. .................................... 514/649; 514/315; 514/317; 514/415; 514/427; 514/443; 514/461; 514/469; 514/471; 546/229; 549/49; 549/55; 549/74; 549/469; 549/491; 548/511; 548/560; 564/383; 568/335; 568/775
[58] Field of Search ............... 514/649, 315, 317, 415, 514/427, 443, 461, 469, 471; 546/429; 549/89, 55, 74, 69, 491; 548/511, 560; 564/383; 568/335, 778

[56] References Cited

PUBLICATIONS

Mitra et al., "Reagents for the Cross-Linking of Proteins by Equilibrium Transfer Alkylation", Journal of the American Chemical Society, vol. 101, No. 11, May 23, 1979, pp. 3097-3110.

*Primary Examiner*—Paul J. Killos

[57] ABSTRACT

Compounds of the formula

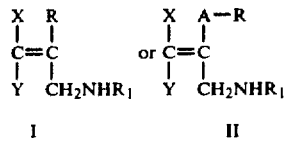

wherein:
R is phenyl, phenyl monosubstituted, disubstituted, or trisubstituted by ($C_1$-$C_8$) alkyl, ($C_1$-$C_8$)alkoxy, hydroxy, chlorine, bromine, iodine, fluorine, trifluoromethyl, nitro, ($C_1$-$C_6$)alkylcarbonyl, benzoyl, or phenyl; 1-, or 2-naphthyl; 1, 2-, or 3-indenyl; 1-, 2-, or 9-fluorenyl; 1-, 2-, or 3-piperidinyl; 2- or 3-pyrrolyl; 2- or 3-thienyl; 2- or 3-furanyl; 2- or 3-indolyl; 2- or 3-thianaphthenyl; or 2- or 3-benzofuranyl;
$R_1$ is hydrogen, ($C_1$-$C_8$)alkyl, benzyl, or phenethyl;
X and Y independently, are hydrogen, fluorine, chlorine, or bromine; and
A is a divalent radical of the formula:

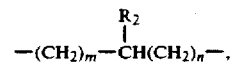

wherein $R_2$ is hydrogen, methyl, or ethyl, and m and n, independently, are an integer from 0 to 4, provided than m+n cannot be greater than 4; —$(CH_2)_p$—D—$(CH_2)_q$—, wherein D is oxygen, or sulfur, p is an integer from 2 to 4, and q is an integer from 0 to 2, provided that p+q cannot be greater than 4; or —$(CH_2)_r$CH=CH$(CH_2)_s$—, wherein r is an integer from 1 to 3 and s is an integer from 0 to 2, provided that r+s cannot be greater than 3;

or a non-toxic, pharmaceutically-acceptable acid addition salt thereof; provided that when each of X and Y in Formula I is hydrogen, R cannot be phenyl;
are MAO inhibitors useful for treating depression. Processes and intermediates for preparing the compounds of Formula I or II are also described.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 52–65, 66, 67 and 68 is confirmed.

Claims 14, 15, 42 and 43 are cancelled.

Claims 1, 4, 13, 16, 32, 41, 44, 45 are determined to be patentable as amended.

Claims 2, 3, 5–12, 17–31, 33–40, 46–51, dependent on an amended claim, are determined to be patentable.

1. A compound of the formula:

$$\begin{array}{ccc} X & R & \\ | & | & \\ C=C & \text{or} & C=C \\ | & | & \\ Y & CH_2NHR_1 & \end{array} \quad \begin{array}{cc} X & A-R \\ | & | \\ C=C & \\ | & | \\ Y & CH_2NHR_1 \end{array}$$

I                   II wherein:

(a) X is fluorine and Y is hydrogen,
(b) Y is fluorine and X is hydrogen, or
(c) X is fluorine and Y is fluorine;

R is phenyl; phenyl monosubstituted, disubstituted, or trisubstituted by $C_1$–$C_8$alkyl, $C_1$–$C_8$alkoxy, hydroxy, chlorine, bromine, iodine, fluorine, trifluoromethyl, [nitro, $C_1$–$C_6$alkylcarbonyl, benzoyl,] or phenyl; 1- or 2-naphthyl; [1-, 2-, or 3-indenyl; 1-, 2-, or 9-fluorenyl; 1-, 2-, or 3-piperidinyl; 2- or 3-pyrrolyl; 2- or 3-thienyl; 2- or 3-furanyl; 2- or 3-indolyl; 2- or 3-thianaphthenyl; or 2- or 3-benzofuranyl;]

$R_1$ is hydrogen [,] or $C_1$–$C_8$alkyl [, benzyl, or phenethyl]; and

A is a divalent radical of the formula:

$$-(CH_2)_m-\overset{R_2}{\underset{|}{CH}}(CH_2)_n-,$$

wherein $R_2$ is hydrogen, methyl, or ethyl, and m and n, independently, are an integer from 0 to 4, provided that m+n cannot be greater than 4; —$(CH_2)_p$—D—$(CH_2)_q$—, wherein D is oxygen or sulfur, p is an integer from 2 to 4, and q is an integer from 0 to 2, provided that p+q cannot be greater than 4; or —$(CH_2)_r$-CH=CH$(CH_2)_s$—, wherein r is an integer from 1 to 3 and s is an integer from 0 to 2, provided that r+s cannot be greater than 3; or a non-toxic, pharmaceutically acceptable acid addition salt thereof.

4. A compound as defined in claim 2 wherein R is phenyl monosubstituted, disubstituted, or trisubstituted by ($C_1$–$C_8$)alkyl, ($C_1$–$C_8$)alkoxy, hydroxy, chlorine, bromine, iodine, fluorine, trifluoromethyl, [nitro, ($C_1$–$C_8$)alkylcarbonyl, benzoyl,] or phenyl.

13. A compound as defined in claim 2 wherein R is 1- or 2-naphthyl [; 1-, 2-, or 3-indenyl; 1-, 2-, or 9-fluorenyl; 1-, 2-, or 3-piperidinyl; 2- or 3-pyrrolyl; 2- or 3-thienyl; 2- or 3-furanyl; 2- or 3-indolyl; 2- or 3-thianaphthenyl; or 2- or 3-benzofuranyl].

16. A compound as defined in claim 2, 3, 4, 5, 6, 7, 8, 9, 10, 11, 12, *or* 13 [, 14, or 15] wherein:

(a) X is hydrogen and Y is fluorine; or
(b) X is fluorine and Y is hydrogen.

32. A compound as defined in claim 30 wherein R is phenyl monosubstituted, disubstituted, or trisubstituted by ($C_1$–$C_8$)alkyl, ($C_1$–$C_8$)alkoxy, hydroxy, chlorine, bromine, iodine, fluorine, trifluoromethyl, [nitro, ($C_1$–$C_8$)alkylcarbonyl, benzoyl,] or phenyl.

41. A compound as defined in claim 30 wherein R is 1- or 2-naphthyl [; 1-, 2-, 3-indenyl; 1-, 2-, or 9-fluorenyl; 1-, 2-, or 3-piperidinyl; 2- or 3-pirrolyl; 2- or 3-thienyl; 2- or 3-furanyl; 2- or 3-indolyl; 2- or 3-thianaphthenyl; or 2- or 3-benzofuranyl].

44. A compound as defined in claim 30, 31, 32, 33, 34, 35, 36, 37, 38, 39, 40, *or* 41 [, 42, or 43] wherein A is —$CH_2$—.

45. A compound as defined in claim 30, 31, 32, 33, 34, 35, 36, 37, 38, 39, 40, *or* 41 [, 42, or 43] wherein:

(a) X is hydrogen and Y is fluorine; or
(b) X is fluorine and Y is hydrogen.

66. A pharmaceutical composition comprising:

(a) a compound of the formula:

$$\begin{array}{ccc} X & R & \\ | & | & \\ C=C & \text{or} & C=C \\ | & | & \\ Y & CH_2NHR_1 & \end{array} \quad \begin{array}{cc} X & A-R \\ | & | \\ C=C & \\ | & | \\ Y & CH_2NHR_1 \end{array}$$

I                   II wherein:

(a) X is fluorine and Y is hydrogen,
(b) Y is fluorine and X is hydrogen, or
(c) X if fluorine and Y is fluorine;

R is phenyl; phenyl monosubstituted, disubstituted, or trisubstituted by $C_1$–$C_8$alkyl, $C_1$–$C_8$alkoxy, hydroxy, chlorine, bromine, iodine, fluorine, trifluoromethyl, [nitro, $C_1$–$C_6$alkylcarbonyl, benzoyl,] or phenyl; 1- or 2-naphthyl; [1-, 2-, 3-indenyl; 1-, 2-, or 9-fluorenyl; 1-, 2-, or 3-piperidinyl; 2- or 3-pyrrolyl; 2- or 3-thienyl; 2- or 3-furanyl; 2- or 3-indolyl; 2- or 3-thianaphthenyl; or 2- or 3-benzofuranyl;]

$R_1$ is hydrogen [,] *or* $C_1$–$C_8$alkyl [, benzyl, or phenethyl]; and A is a divalent radical of the formula:

$$-(CH_2)_m-\overset{R_2}{\underset{|}{CH}}(CH_2)_n-,$$

wherein $R_2$ is hydrogen, methyl, or ethyl, and m and n, independently, are an integer from 0 to 4, provided that m+n cannot be greater than 4; —$(CH_2)_p$—D—$(CH_2)_q$—, wherein D is oxygen or sulfur, p is an integer from 2 to 4, and q is an integer from 0 to 2, provided that p+q cannot be greater than 4; or —$(CH_2)_r$-CH=CH$(CH_2)_s$—, wherein r is an integer from 1 to 3 and s is an integer from 0 to 2, provided that r+s cannot be greater than 3; or a non-toxic, pharmaceutically acceptable acid addition salt thereof; *and*

(b) *a pharmaceutically acceptable carrier.*

\* \* \* \* \*